(12) United States Patent
Li et al.

(10) Patent No.: US 8,063,021 B2
(45) Date of Patent: Nov. 22, 2011

(54) KETOLIDE ANTI-INFECTIVE COMPOUNDS

(75) Inventors: Yong Li, Palo Alto, CA (US); Yandong Li, San Leandro, CA (US); Yan Zhu, Foster City, CA (US); Chaitan Khosla, Palo Alto, CA (US); David C. Myles, Kensington, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 2023 days.

(21) Appl. No.: 10/883,317

(22) Filed: Jun. 30, 2004

(65) Prior Publication Data

US 2005/0272672 A1    Dec. 8, 2005

Related U.S. Application Data

(63) Continuation-in-part of application No. 10/347,512, filed on Jan. 17, 2003, now Pat. No. 6,939,861.

(51) Int. Cl.
*A61K 31/70* (2006.01)
*C07H 17/08* (2006.01)

(52) U.S. Cl. .......................... 514/29; 536/7.4
(58) Field of Classification Search .............. 536/7.4
See application file for complete search history.

(56) References Cited

U.S. PATENT DOCUMENTS

| | | | |
|---|---|---|---|
| 4,474,768 A | 10/1984 | Bright | 424/180 |
| 5,141,926 A | 8/1992 | Weber et al. | 514/29 |
| 5,510,118 A | 4/1996 | Bosch et al. | 424/489 |
| 5,527,780 A | 6/1996 | Agouridas et al. | 514/29 |
| 5,534,270 A | 7/1996 | De Castro | 424/490 |
| 5,662,883 A | 9/1997 | Bagchi et al. | 424/9.4 |
| 6,043,226 A | 3/2000 | Lundy et al. | 514/29 |
| 6,100,404 A | 9/2000 | Agouridas et al. | 546/274 |
| 6,124,269 A | 9/2000 | Phan et al. | 514/29 |
| 6,395,710 B1 | 5/2002 | Chu et al. | 514/29 |
| 6,399,582 B1 | 6/2002 | Hlasta et al. | 514/29 |
| 6,451,768 B1 | 9/2002 | Chu | 514/29 |
| 6,458,771 B1 | 10/2002 | Hlasta et al. | 514/29 |
| 6,514,944 B2 | 2/2003 | Chu | 514/29 |
| 6,562,795 B2 | 5/2003 | Ashley et al. | 514/29 |
| 6,590,083 B1 | 7/2003 | Hlasta et al. | 536/7.4 |
| 6,593,302 B2 | 7/2003 | Chu et al. | 514/29 |
| 6,762,168 B2 | 7/2004 | Chu | 514/29 |
| 6,794,366 B2 | 9/2004 | Chu et al. | 514/29 |
| 6,939,861 B2 * | 9/2005 | Ashley et al. | 514/29 |
| 2002/0094962 A1 | 7/2002 | Ashley et al. | 514/28 |
| 2002/0192709 A1 | 12/2002 | Carreras et al. | 534/7.1 |
| 2003/0199458 A1 | 10/2003 | Ashley et al. | 514/29 |

FOREIGN PATENT DOCUMENTS

| | | |
|---|---|---|
| WO | WO 02/32918 A2 | 4/2002 |
| WO | WO 03/061671 A1 | 7/2003 |
| WO | WO 2004/019879 A2 | 3/2004 |

OTHER PUBLICATIONS

Bryskier and Denis, Ketolides: novel antibacterial agents designed to overcome resistance to erythromycin A within gram-positive cocci. In *Macrolide Antibiotics*; Schönfeld and Kirst, eds.; Birkhauser Verlag: Basel, Switzerland, 2002; pp. 97-140.
Dorow et al., *J. Org. Chem.* 60, 4986-4987 (1995), "A Novel Preparation of Scalemic N-Methyl-α-amino Acids".
Nicolaou et al., *J. Am. Chem. Soc.* 124 (10), 2212-2220 (2002), "Iodine (V) Reagents in Organic Synthesis. Part 1. Synthesis of Polycyclic Heterocycles via Dess-Martin Periodinane Mediated Cascade Cyclization: Generality, Scope, and Mechanism of the Reaction".

\* cited by examiner

*Primary Examiner* — Elli Peselev
(74) *Attorney, Agent, or Firm* — Ying Wang

(57) ABSTRACT

Compounds according to formula I

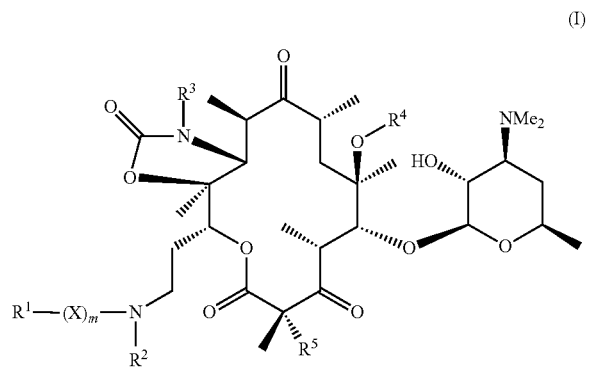

wherein m is 0 or 1;
X is

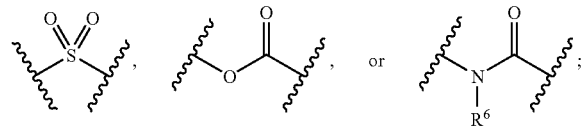

and $R^1$, $R^2$, $R^3$ $R^4$, and $R^5$ are as defined herein, are useful as anti-infective agents.

20 Claims, 9 Drawing Sheets

KETOLIDE ANTI-INFECTIVE COMPOUNDS

CROSS-REFERENCE TO RELATED APPLICATIONS

This application is a continuation-in-part of application Ser. No. 10/347,512, filed Jan. 17, 2003, now U.S. Pat. No. 6,939,861, the disclosure of which is incorporated by reference.

BACKGROUND OF THE INVENTION

1. Field of the Invention

This invention relates to ketolide anti-infective compounds and methods for their preparation and use.

2. Description of Related Art

The erythromycins are a family of macrolide antibiotics made by the fermentation of the Actinomycetes *Saccharopolyspora erythraea* (formerly *Streptomyces erythreus*). Erythromycin A, a commonly used antibiotic, is the best known and most important member of the family.

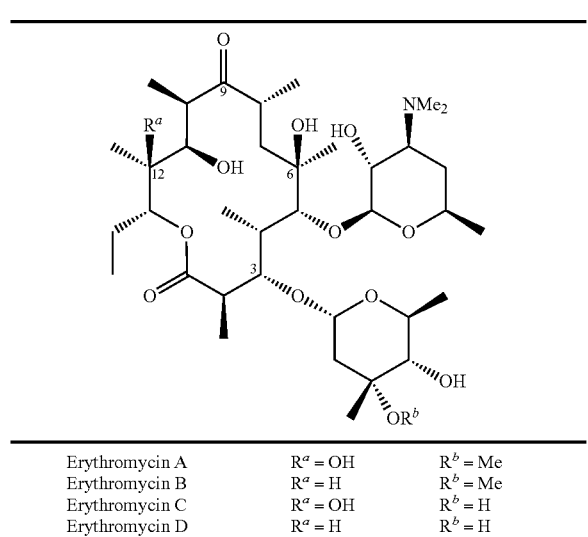

| | | |
|---|---|---|
| Erythromycin A | $R^a$ = OH | $R^b$ = Me |
| Erythromycin B | $R^a$ = H | $R^b$ = Me |
| Erythromycin C | $R^a$ = OH | $R^b$ = H |
| Erythromycin D | $R^a$ = H | $R^b$ = H |

Subsequent to the initial discovery of the erythromycins, considerable research efforts have been expended towards the development of antibiotics based on the erythromycin scaffold, with the objective of improving one aspect or another of its activity profile or other characteristic relevant to its use as an antibiotic. The approaches have ranged from the bioengineering of producing organisms to engender biosynthesis of new erythromycin-like compounds to post-biosynthesis chemical modification of an erythromycin to make semi-synthetic antibiotics to a combination of the two.

The serendipitous discovery that erythromycin A has activity as an agonist of the motilin receptor spurred another spate of research activity into erythromycin derivatives. (The binding of motilin, the natural ligand, to the motilin receptor stimulates gastrointestinal motility.) This time, the research was aimed identifying erythromycin derivatives for treatment of gastrointestinal motility disorders, such compounds being referred to as motilides. Ironically, a key concern in designing a motilide is the elimination of antibacterial activity, lest it induce antibiotic resistant in the bacteria populating the gastrointestinal tract.

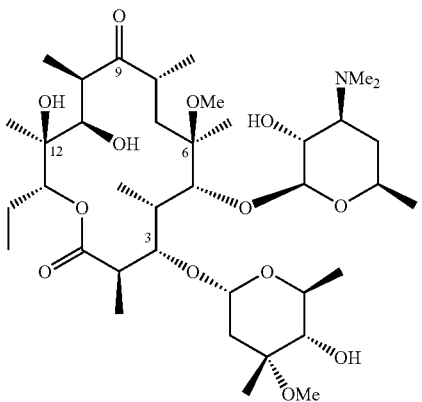

Clarithromycin

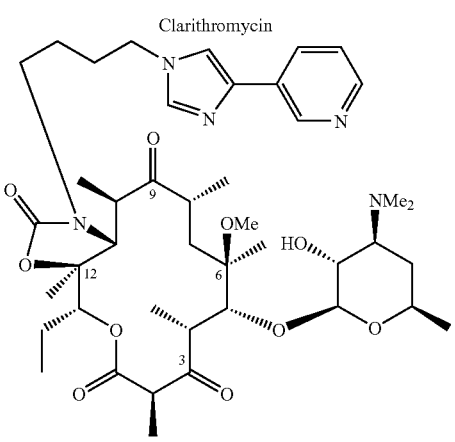

Telithromycin

Among the semi-synthetic erythromycin antibiotics, clarithromycin is made by methylation the 6-hydroxyl group of erythromycin A and has improved acid stability, making it more suitable for oral administration. Telithromycin is another semi-synthetic erythromycin antibiotic, in which a 3-keto group has replaced the 3-cladinose group and the 11,12-positions have been bridged by an N-substituted carbamate moiety. Telithromycin displays good activity against gram-positive cocci having resistance to erythromycin A and, like clarithromycin, has improved acid stability. Generically, telithromycin and other 3-keto erythromycin compounds are referred to as the ketolides. For a review on ketolides, see Bryskier and Denis, "Ketolides: novel antibacterial agents designed to overcome resistance to erythromycin A with gram-positive cocci," in Schonfeld and Kirst, eds., *Macrolide Antibiotics*, pp. 97-140 (Birkhauser Verlag, Basel, Switzerland, 2002).

Other disclosures relating to erythromycin-derived semi-synthetic compounds include: Bright, U.S. Pat. No. 4,474,768 (1984); Weber et al. U.S. Pat. No. 5,141,926 (1992); Agouridas et al. U.S. Pat. No. 5,527,780 (1996); Lundy et al. U.S. Pat. No. 6,043,226 (2000); Agouridas et al., U.S. Pat. No. 6,100,404 (2000); Phan et al., U.S. Pat. No. 6,124,269 (2000); Chu et al., U.S. Pat. No. 6,395,710 B1 (2002); Hlasta et al., U.S. Pat. No. 6,399,582 B1 (2002); Chu, U.S. Pat. No. 6,451,768 B1 (2002); Hlasta et al., U.S. Pat. No. 6,458,771 B1 (2002); Chu, U.S. Pat. No. 6,514,944 B2 (2003); Ashley et al., U.S. Pat. No. 6,562,795 (2003); Hlasta et al., U.S. Pat. No. 6,590,083 B1 (2003); Hlasta et al., WO 02/32918 A2 (2002);

BRIEF SUMMARY OF THE INVENTION

In a first embodiment, there is provided a compound having a structure according to formula I

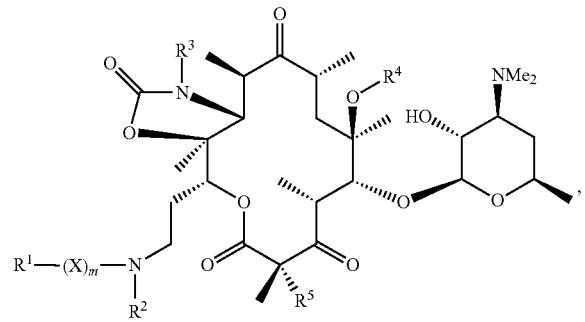

(I)

and the pharmaceutically acceptable salts, esters, solvates, hydrates, and prodrug forms thereof,
wherein
m is 0 or 1;
X is

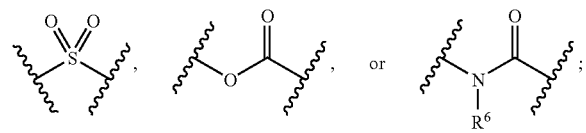

$R^1$ is $C_1$-$C_5$ alkyl, $C_2$-$C_5$ alkenyl, $C_2$-$C_5$ alkynyl, aryl, heterocyclo, (heterocyclo)alkyl, biaryl, arylalkyl, arylalkenyl, arylalkynyl, biarylalkyl, biarylalkenyl, or biarylalkynyl;

$R^2$ is H, $C_1$-$C_5$ alkyl, $C_2$-$C_5$ alkenyl, $C_2$-$C_5$ alkynyl, arylalkyl, arylalkenyl, arylalkynyl, biarylalkyl, biarylalkenyl, or biarylalkynyl; or, when m is 0, $R^1$ and $R^2$ may combine with the nitrogen to which they are commonly bonded to form a 4, 5, 6, or 7-membered heterocyclic ring structure;

$R^3$ and $R^4$ are independently H, $C_1$-$C_5$ alkyl, $C_2$-$C_5$ alkenyl, $C_2$-$C_5$ alkynyl, arylalkyl, arylalkenyl, arylalkynyl, biarylalkyl, biarylalkenyl, or biarylalkynyl;

$R^5$ is H or F; and $R^6$ is H, $C_1$-$C_5$ alkyl, $C_2$-$C_5$ alkenyl, or $C_2$-$C_5$ alkynyl, or $R^1$ and $R^6$ may combine with the nitrogen to which they are commonly bonded to form a 4, 5, 6, or 7-membered heterocyclic ring structure.

In a second embodiment, there is provided a method of inhibiting the proliferation of a microbial pathogen, comprising contacting the microbial pathogen with an effective amount of a compound of this invention.

In a third embodiment, there is provided a method of treating an infection by a microbial pathogen, comprising administering to a subject suffering from such infection a therapeutically effective amount of a compound of this invention. The subject can be a mammal, especially a human.

In a fourth embodiment, there is provided the use of a compound of this invention for the preparation of a medicament for treating a microbial infection.

In a fifth embodiment, there is provided a pharmaceutical formulation comprising a compound of this invention and an excipient.

BRIEF DESCRIPTION OF THE DRAWING(S)

DETAILED DESCRIPTION OF THE INVENTION

Definitions

Figure 1:
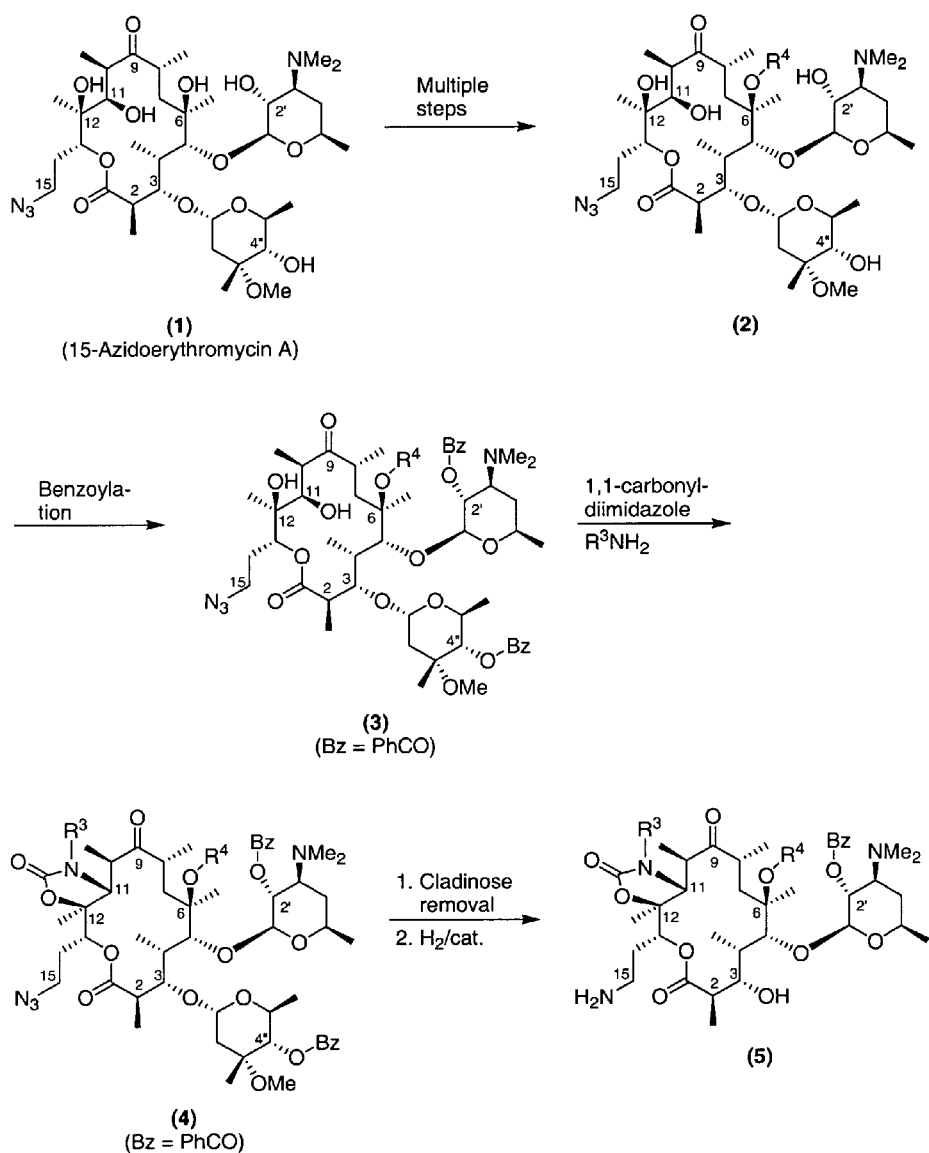
FIG. 1 shows a scheme for synthesizing intermediates useful for making compounds of this invention.

"Alkyl" means an optionally substituted straight or branched chain hydrocarbon moiety having the specified number of carbon atoms in its longest chain portion (e.g., as in "$C_3$ alkyl," "$C_1$-$C_5$ alkyl," or "$C_1$ to $C_5$ alkyl," the latter two phrases referring to an alkyl group having from 1 to 5 carbon atoms in the longest chain portion) or, where the number of carbon atoms is not specified, from 1 to 4 carbon atoms in the longest chain portion.

"Alkenyl" means an optionally substituted straight or branched chain hydrocarbon moiety having at least one carbon-carbon double bond and the specified number of carbon atoms in its longest chain portion (e.g., as in "$C_3$ alkenyl," "$C_2$-$C_5$ alkenyl," or "$C_2$ to $C_5$ alkenyl," the latter two phrases referring to an alkenyl group having from 2 to 5 carbon atoms in the longest chain portion) or, where the number of carbon atoms is not specified, from 2 to 4 carbon atoms in the longest chain portion.

"Alkynyl" means an optionally substituted straight or branched chain hydrocarbon moiety having at least one carbon-carbon triple bond and the specified number of carbon atoms in its longest chain portion (e.g., as in "$C_3$ alkenyl," "$C_2$-$C_5$ alkynyl," or "$C_2$ to $C_5$ alkynyl," the latter two phrases referring to an alkynyl group having from 2 to 5 carbon atoms in the longest chain portion) or, where the number of carbon atoms is not specified, from 2 to 4 carbon atoms in the longest chain portion.

"Aryl" means an optionally substituted aromatic monocyclic, fused bicyclic, or fused polycyclic hydrocarbon or heterocyclic group having 1 to 20 carbon atoms in the ring portion(s), such as phenyl, naphthyl, pyrrolyl, indolyl, pyrazolyl, pyrazolinyl, imidazolyl, oxazolyl, isoxazolyl, thiazolyl, thiadazolyl, isothiazolyl, furyl, thienyl, oxadiazolyl, pyridinyl, N-oxo-pyridyl, pyrazinyl, pyrimidinyl, pyridazinyl, tetrazinyl, triazinyl, triazolyl, benzothiazolyl, benzoxazolyl, benzothienyl, quinolinyl, quinolinyl-N-oxide, isoquinolinyl, benzimidazolyl, benzofuryl, chromonyl, coumarinyl, cinnolinyl, quinoxalinyl, indazolyl, benzisothiazolyl, benzisoxazolyl, benzodiazinyl, tetrazolyl, benzofurazanyl, benzothiopyranyl, benzpyrazolyl, indolinyl, isochromanyl, isoindolinyl, naphthyridinyl, phthalazinyl, purinyl, quinazolinyl, and the like.

"Arylalkyl," "(heterocyclo)alkyl," "arylalkenyl," "arylalkynyl," "biarylalkyl," and the like mean an aryl, heterocyclo, or biaryl group, as the case may be, bonded directly to an alkyl, alkenyl, or alkynyl moiety, as the case may be, with the open (unsatisfied) valence at the alkyl, alkenyl, or alkynyl group, for example as in benzyl, phenethyl, N-imidazoylethyl, N-morpholinoethyl, and the like.

"Biaryl" means a combination of two nonfused aryl groups directly bonded to each other. Exemplary biaryl groups include biphenyl, furylphenyl, phenylfuryl, thienylphenyl, phenylthienyl, pyridylphenyl, phenylpyridyl, furylpyridyl, pyridylfuryl, pyrrolylpyridyl, pyridylthienyl, isoxazolylthienyl, isoxazolylphenyl, and the like.

"Cycloalkyl" means an optionally substituted, saturated or unsaturated, non-aromatic cyclic hydrocarbon ring system, preferably containing 1 to 3 rings and 3 to 7 carbons per ring which may be further fused with a saturated or unsaturated $C_3$-$C_7$ carbocyclic ring. Exemplary cycloalkyl ring systems include cyclopropyl, cyclobutyl, cyclopentyl, cyclohexyl, cycloheptyl, cyclooctyl, cyclodecyl, cyclododecyl, and adamantyl.

"Halogen," "hal," or "halo" means fluorine, chlorine, bromine or iodine.

"Heterocycle", "heterocyclic," or "heterocyclo" means an optionally substituted, fully saturated or unsaturated, aromatic or nonaromatic ring system, for example, which is a 4 to 7 membered monocyclic, 7 to 11 membered bicyclic, or 10 to 15 membered tricyclic ring system, which has at least one heteroatom in at least one carbon atom-containing ring. "Heteroaryl" means a heterocycle in which the ring system is aryl. Each ring of the heterocyclic group containing a heteroatom may have 1, 2 or 3 heteroatoms selected from N, O and S, where the N and S optionally may be oxidized and the N optionally may be quaternized. Exemplary monocyclic heterocyclic ring systems include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, tetrazolyl, triazinyl, and triazolyl, and the like. Preferred heterocyclo groups include pyridinyl, morpholinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, piperazinyl, and piperidinyl.

Where it is indicated that a group may be substituted, for example by use of "substituted or unsubstituted" or "optionally substituted" phrasing, such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, heterocycloalkyl, cycloalkylamino, heterocycloamino, dialkylamino, alkanoylamino, thio, alkylthio, cycloalkylthio, heterocyclothio, ureido, nitro, cyano, carboxy, caroboxylalkyl, carbamyl, alkoxycarbonyl, alkylthiono, arylthiono, alkylsulfonyl, sulfonamindo, aryloxy, and the like, in addition to those specified herein. Preferably, the substituent(s) for alkyl, alkenyl, and alkynyl moieties are from one to three in number and are independently selected from N-pyrrolidinyl, N-morpholinyl, N-azetidinyl, hydroxyl, halo, alkoxyl, cyano, amino, alkylamino, and dialkylamino. Preferably, the substituent(s) for aryl, cycloalkyl, and heterocycloalkyl moieties are from one to three in number and are independently selected from alkyl, alkenyl, alkynyl, hydroxyalkyl, haloalkyl, hydroxyl, halo, alkoxyl, cyano, aminoalkyl, alkylaminoalkyl, dialkylaminoalkyl, amino, alkylamino, and dialkylamino.

"Pharmaceutically acceptable salts" means salts of the active compounds that are prepared with relatively nontoxic acids or bases, depending on the particular substituents found on the compounds described herein. When a compound contains a relatively acidic functionality, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound contains a relatively basic functionality, an acid addition salt can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogen-phosphoric, sulfuric, monohy-drogen-sulfuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, fumaric, mandelic, phthalic, benzenesulfonic, p-tolylsulfonic, citric, tartaric, methane-sulfonic, lactobionic, and the like. Also included are salts of amino acids such as arginate and the like, and salts of organic acids like glucuronic or galactunoric acids and the like. Where a compound contains both basic and acidic functionalities, they can be converted into either a base or an acid addition salt.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in *Design of Prodrugs*, Bundgaard, ed., Elsevier, 1985.

"Pharmaceutically acceptable ester" means an ester that hydrolyzes in vivo (for example in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

"Therapeutically effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Where a range is stated, as in "$C_1$ to $C_5$ alkyl" or "5 to 10%," such range includes the end points of the range.

Compounds

In a first preferred embodiment, $R^3$ is H, $R^4$ is methyl, and $R^5$ is H, corresponding to a compound represented by formula Ia. More preferably, m is 1.

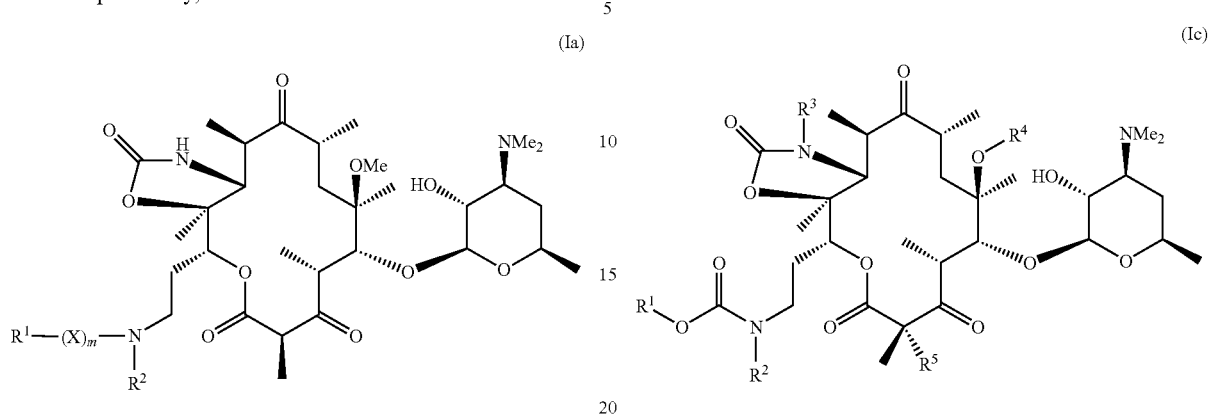

In a second preferred embodiment, m is 1 and X is

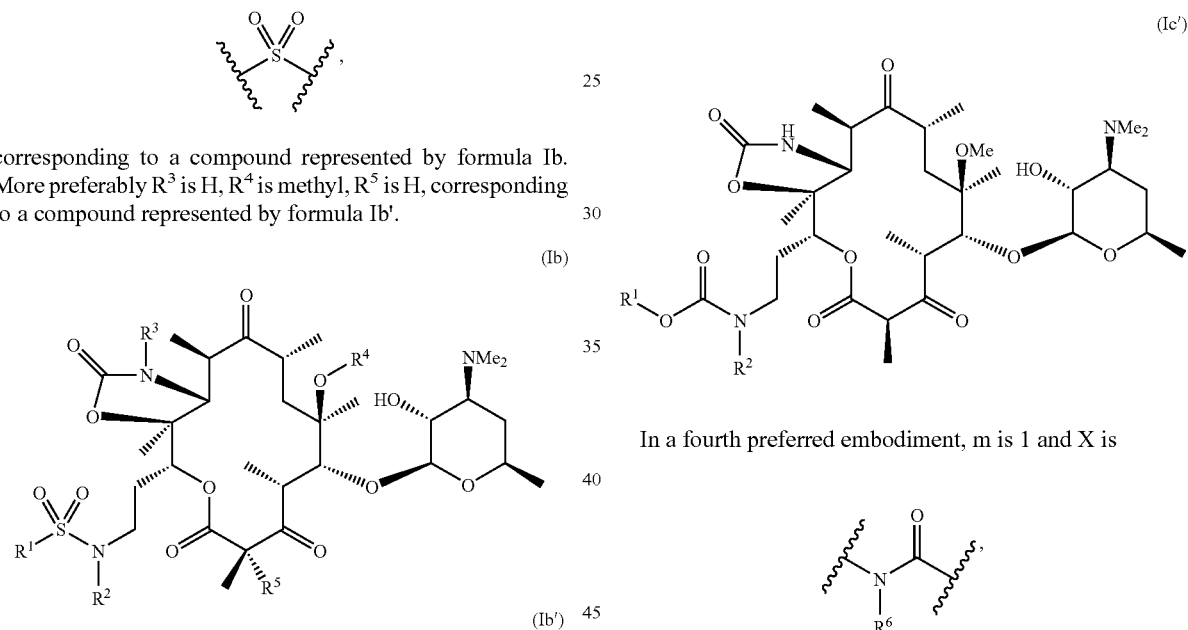

corresponding to a compound represented by formula Ib. More preferably $R^3$ is H, $R^4$ is methyl, $R^5$ is H, corresponding to a compound represented by formula Ib'.

In a third preferred embodiment, m is 1 and X is

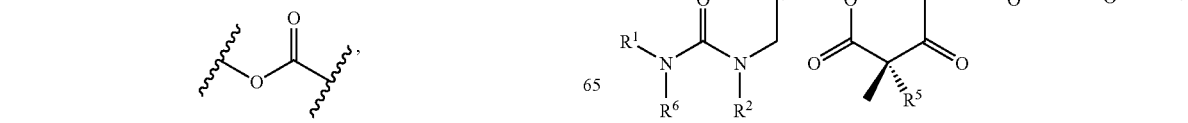

corresponding to a compound represented by formula Ic. More preferably, $R^3$ is H, $R^4$ is methyl, $R^5$ is H, corresponding to a compound represented by formula Ic'.

In a fourth preferred embodiment, m is 1 and X is corresponding to a compound represented by formula Id. More preferably, $R^3$ is H, $R^4$ is methyl, $R^5$ is H, corresponding to a compound represented by formula Id'.

(Id')

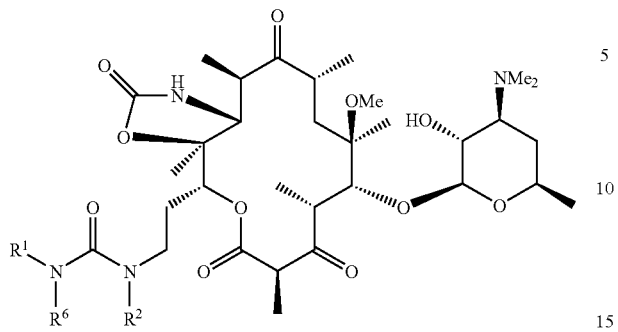

In a fifth preferred embodiment, m is 0 (i.e., X is absent and the adjacent nitrogen is directly bonded to $R^1$), corresponding to a compound represented by formula Ie. More preferably, $R^3$ is H, $R^4$ is methyl, and $R^5$ is H, corresponding to a compound represented by formula Ie'.

(Ie)

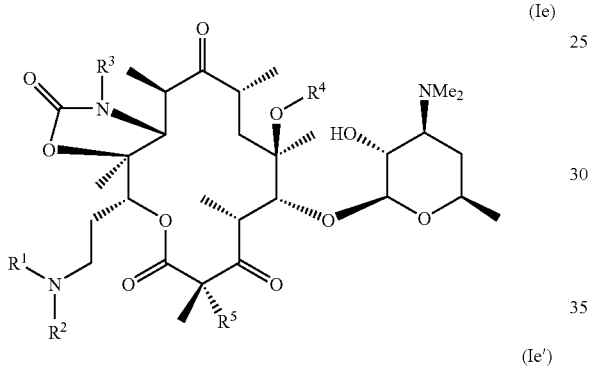

(Ie')

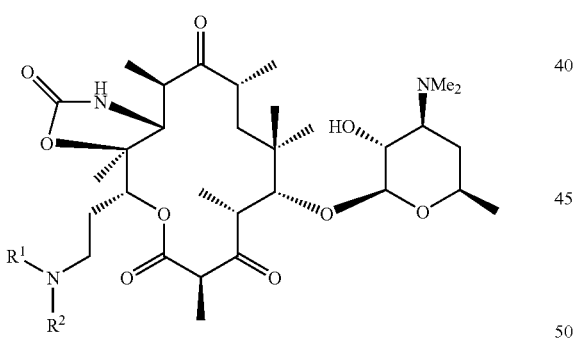

In the foregoing compounds of formula Ia-Ie and Ib'-Ie', $R^1$, $R^2$, $R^3$ (where present), $R^4$ (where present) and $R^6$ (where present) have the meanings assigned in the BRIEF SUMMARY OF THE INVENTION section. Preferably, $R^2$ is H in the compounds of formulae Ib, Ib', Ic, Ic', Id, and Id'.

Preferably, $R^1$ is $C_1$-$C_5$ alkyl, aryl, biaryl, arylalkyl, or biarylalkyl, or, when m is 0, combines with $R^2$ and the nitrogen to which they are commonly bonded to form a 4, 5, 6, or 7-membered heterocyclic ring structure. Preferably $R^2$ is H, $C_1$-$C_5$ alkyl, arylalkyl, or biarylalkyl, or, when m is 0, combines with $R^1$ and the nitrogen to which they are commonly bonded to form a 4, 5, 6, or 7-membered heterocyclic ring structure. $R^3$ preferably is H. $R^4$ preferably is methyl. $R^5$ preferably is H.

Where $R^1$ and $R^2$ or $R^1$ and $R^6$ combine to form a 4, 5, 6 or 7 membered heterocyclic ring structure, such heterocyclic ring structure preferably is an azetidinyl, pyrrolidinyl, piperidinyl, or azepanyl ring structure (the first three being especially preferred). The ring structure optionally may be substituted, the substituents preferably being from one to three in number.

Exemplary groups $R^3$ other than H include methyl, allyl, (2-dimethylamino)ethyl,

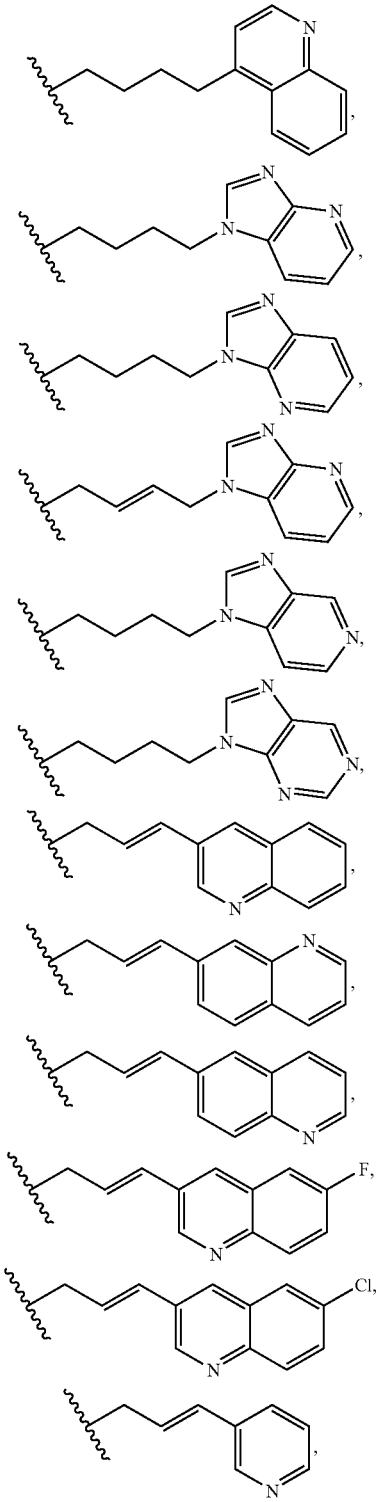

-continued
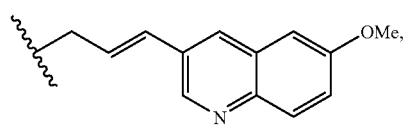
and
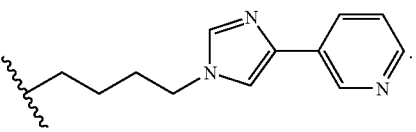
Exemplary groups R⁴ other than H include methyl (preferred), allyl, benzyl, (2-methylamino)ethyl, phenethyl,
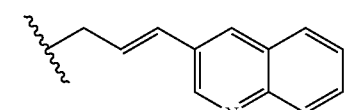,
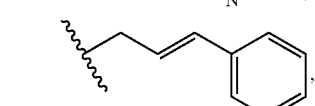,
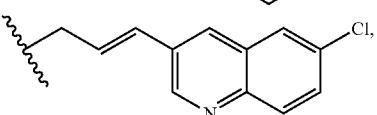,
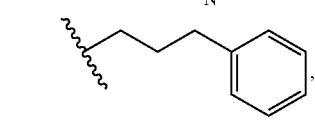,
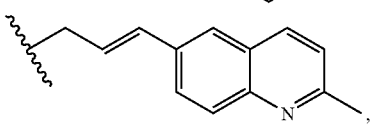,
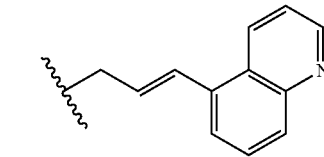,
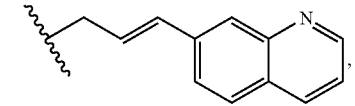,
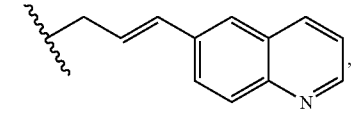,
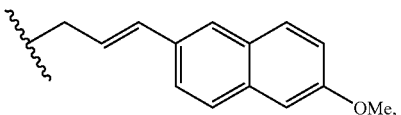,
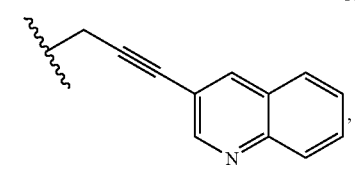,
-continued
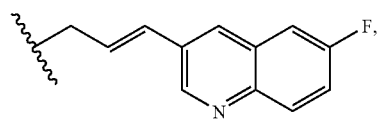,
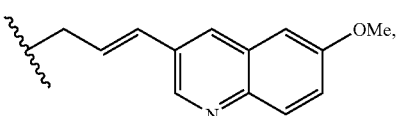,
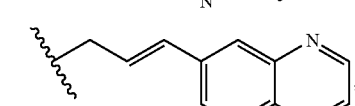,
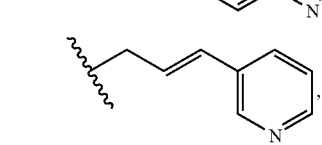,
and
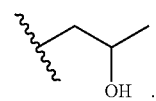.
Illustrative specific compounds according to formula I are given in Table A (R³ is H, R⁴ is methyl, and R⁵ is H):
TABLE A
| Compound | $R^1\!-\!(X)_m\!-\!N\!\begin{smallmatrix}\\ R^2\end{smallmatrix}$ |
|---|---|
| 101 | 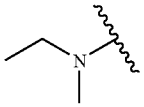 |
| 102 | 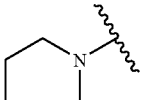 |
| 103 | 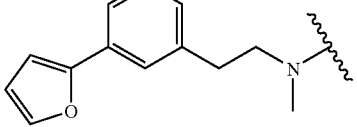 |
| 104 | 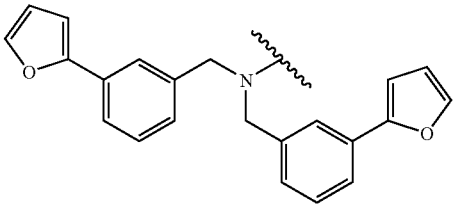 |

TABLE A-continued

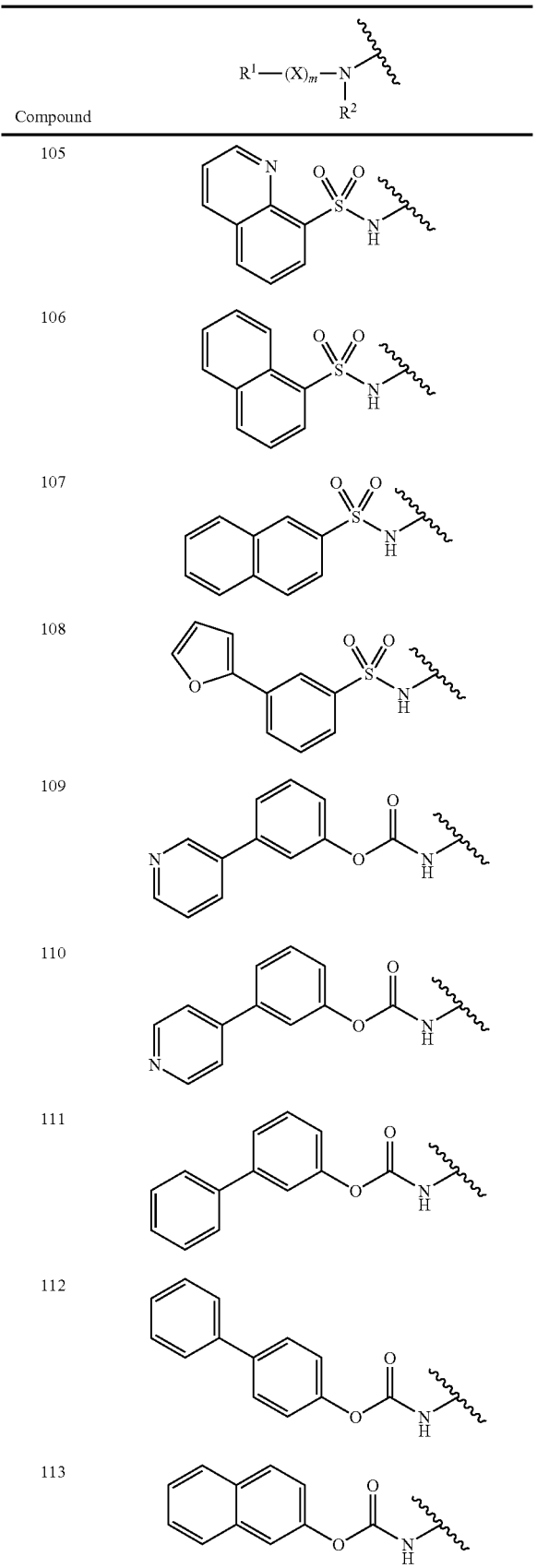

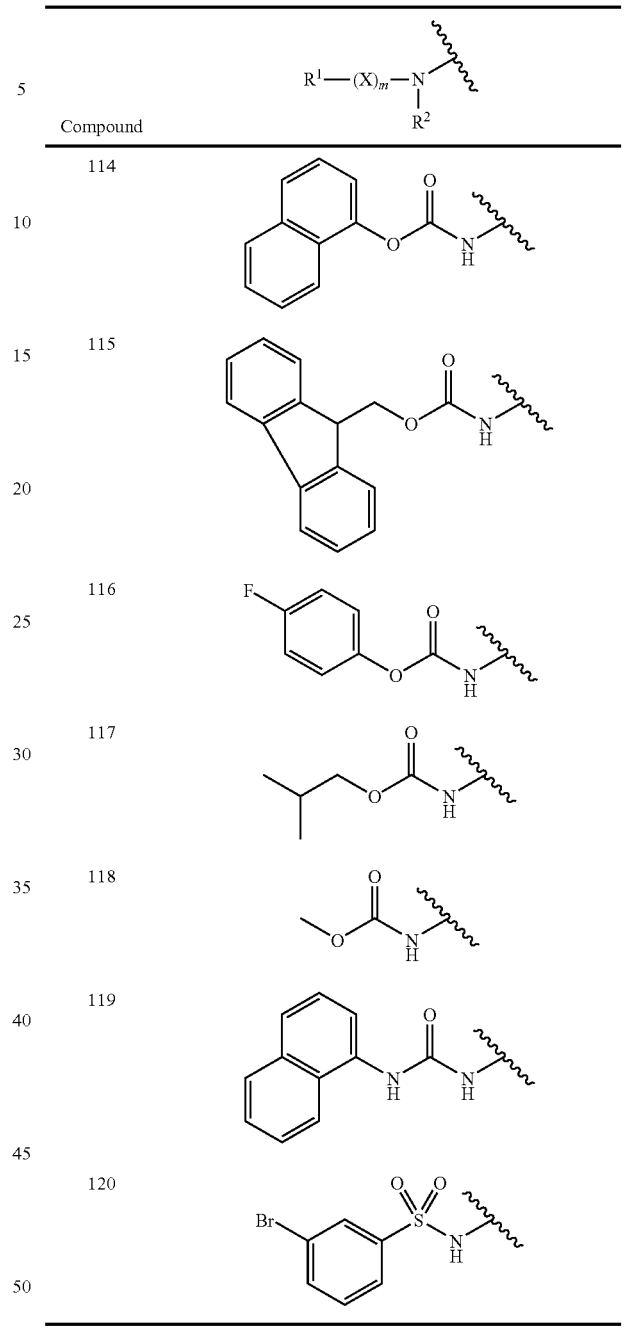

FIG. 1 shows a scheme for the synthesis of amine 5, which is a versatile common intermediate for making compounds of this invention. The starting material is 15-azidoerythromycin A (1), whose preparation is described in Ashley et al., U.S. 2003/0199458 A1 (2003) (hereinafter "Ashley '458"), the disclosure of which is incorporated by reference. 15-Azido-erythromycin A 1 is converted to amine 5 in a multi-step sequence as follows. The 9-keto group is converted to a 9-oxime group with aqueous hydroxylamine and acetic acid. The 9-oxime is protected as a ketal with 1,1-diisopropoxycyclohexane. The 2'- and 4"-hydroxyl groups are then protected with trimethylsilyl chloride, setting the stage for alkylation of the 6'-hydroxyl group with an alkylating agent such as an alkyl halide $R^4$-Hal. The oxime and 2'- and 4"-hydroxyl protecting groups are removed, using aqueous acetic acid-acetonitrile. Deoximation with sodium hydrosulfide yields 6-O-alkyl compound 2.

Benzoylation of 6-O-alkyl compound 2 with benzoic anhydride produces dibenzoyl derivative 3. Ashley '458 describes in detail the conversion of 15-azidoerythromycin 1 to dibenzoyl derivative 3 for the specific instance in which $R^4$ is methyl. Such description may be used as an exemplar for such conversions in general. Alternatively, instead of protecting the 2'- and 4"-hydroxyl groups with a trimethylsilyl group in the preparation of 6-O-alkyl compound 2, these groups can be benzoylated. The benzoyl groups survive the subsequent oxime de-protection and removal steps, leading directly to dibenzoyl derivative 3, saving a synthetic step.

Dibenzoyl derivative 3 is next converted to 11,12-cyclic carbamate 4 by treatment with 1,1-carbonyldiimidazole and by ammonia (as described in Ashley '458) or an amine $R^3NH_2$ (where $R^3$ is other than H, as described in Agouridas et al., U.S. Pat. No. 6,100,404 (2000), incorporated herein by reference). Removal of the 3-cladinose moiety with ethanolic aqueous hydrochloric acid and catalytic (Pd) hydrogenation of the 15-azido group completes the synthesis of amine 5.

Ashley '458 provides a detailed procedure for the synthesis of amine 5 in the specific instance in which $R^3$ is H and $R^4$ is methyl, corresponding to an amine of structure 5a. This procedure may be taken as representative for the synthesis of other amines 5.

(5a)

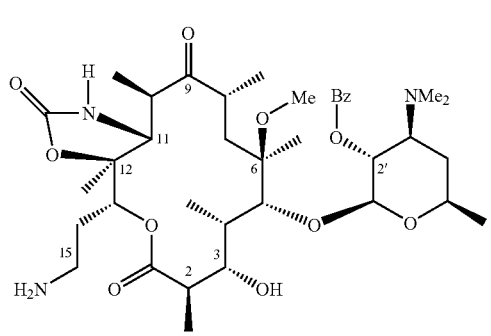

Figure 2:
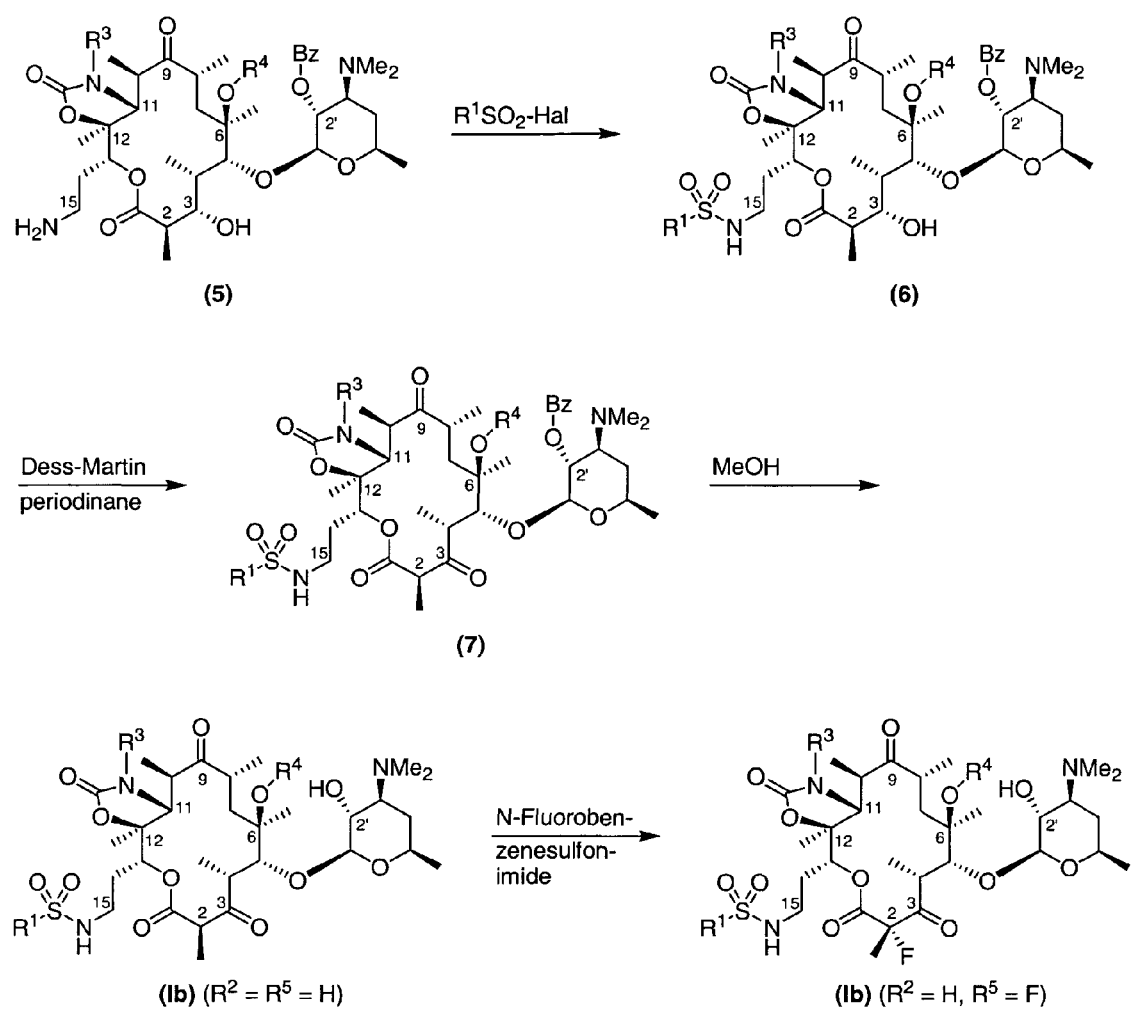
FIGS. 2 through 9 show, either generically or specifically, schemes for making compounds of this invention.

FIG. 2 shows a scheme for the preparation of compounds represented by formula Ib from common intermediate amine 5. Sulfonylation of amine 5 with a sulfonyl halide $R^1SO_2$-Hal provides intermediate sulfonamide 6. Oxidation of the 3-hydroxyl group with Dess-Martin periodinane yields 3-keto sulfonamide 7. Methanolysis of the benzoyl group provides compounds Ib, in the instance in which $R^2$ and $R^5$ are both H. Fluorination with N-fluorobenzenesulfonimide converts the previous product to compounds Ib where $R^5$ is F (see Ashley '458 for an illustrative procedure.) As demonstrated below in the context of compound 108, an $R^1$ group initially introduced by a sulfonylation reaction can be further modified if desired.

Figure 3:
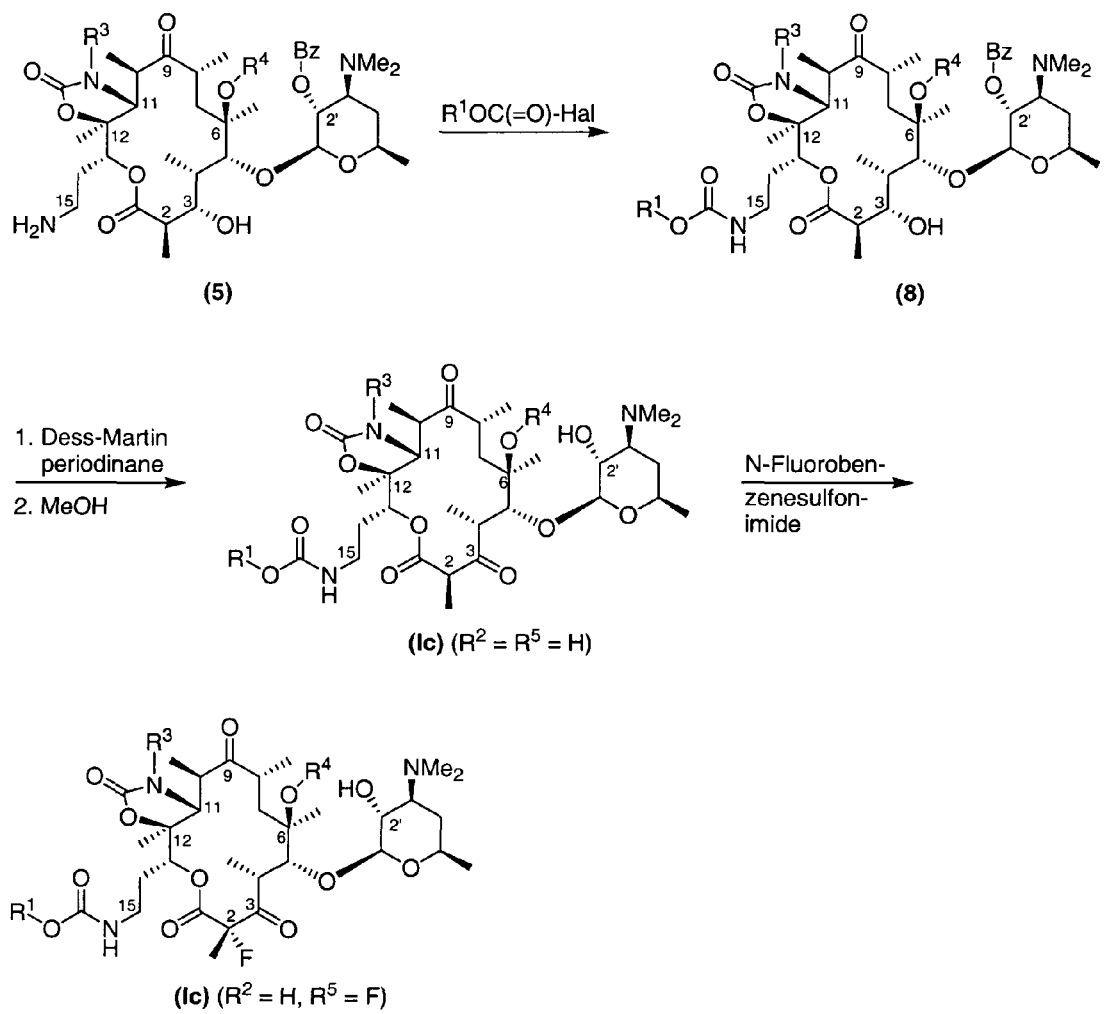

FIG. 3 shows a scheme for preparing compounds represented by formula Ic. Reaction of amine 5 with an oxycarbonyl halide $R^1OC(=O)$Hal produces intermediate carbamate 8, which is converted to compound Ic ($R^5$ equals either H or F) by a sequence of steps analogous to those described above in the context of FIG. 2.

Figure 4:
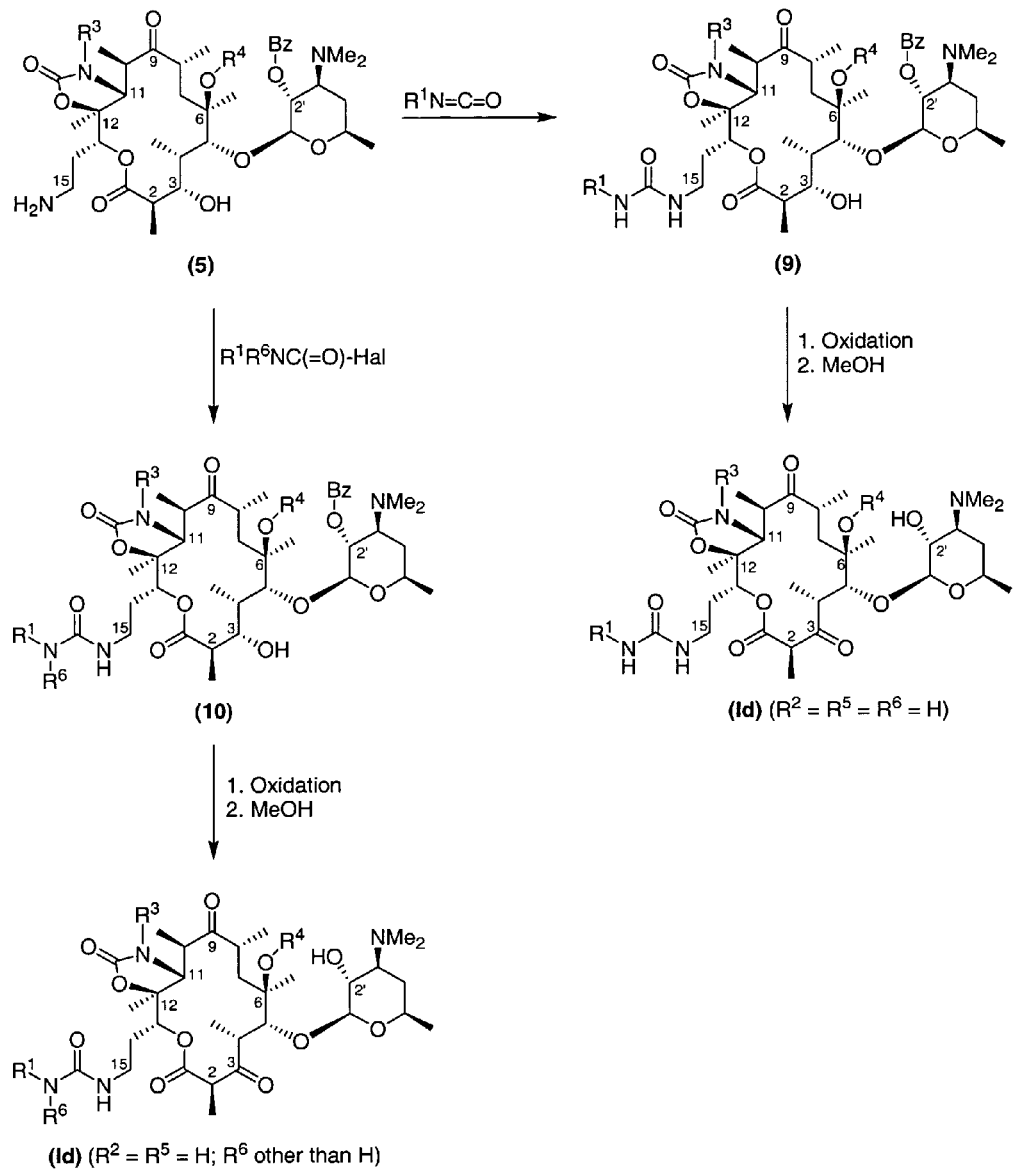

FIG. 4 shows schemes for preparing compounds having a structure according to formula Id. In a first option, reaction of amine 5 with an isocyanate $R^1N=C=O$ produces, after Dess-Martin oxidation and methanolysis of the 2'-benzoyl group, compound Id where $R^2$, $R^5$, and $R^6$ are all H. In a second option, reaction of amine 5 with an N,N-disubstituted carbamyl halide $R^1R^6NC(=O)$Hal produces, again after Dess-Martin oxidation and 2'-benzoyl group removal, compounds Id where $R^6$ is other than H. In each alternative, further conversion of the initial compound Id to the embodiment in which $R^5$ is F can be accomplished by fluorination with N-fluorobenzensulfonimide.

Figure 5:
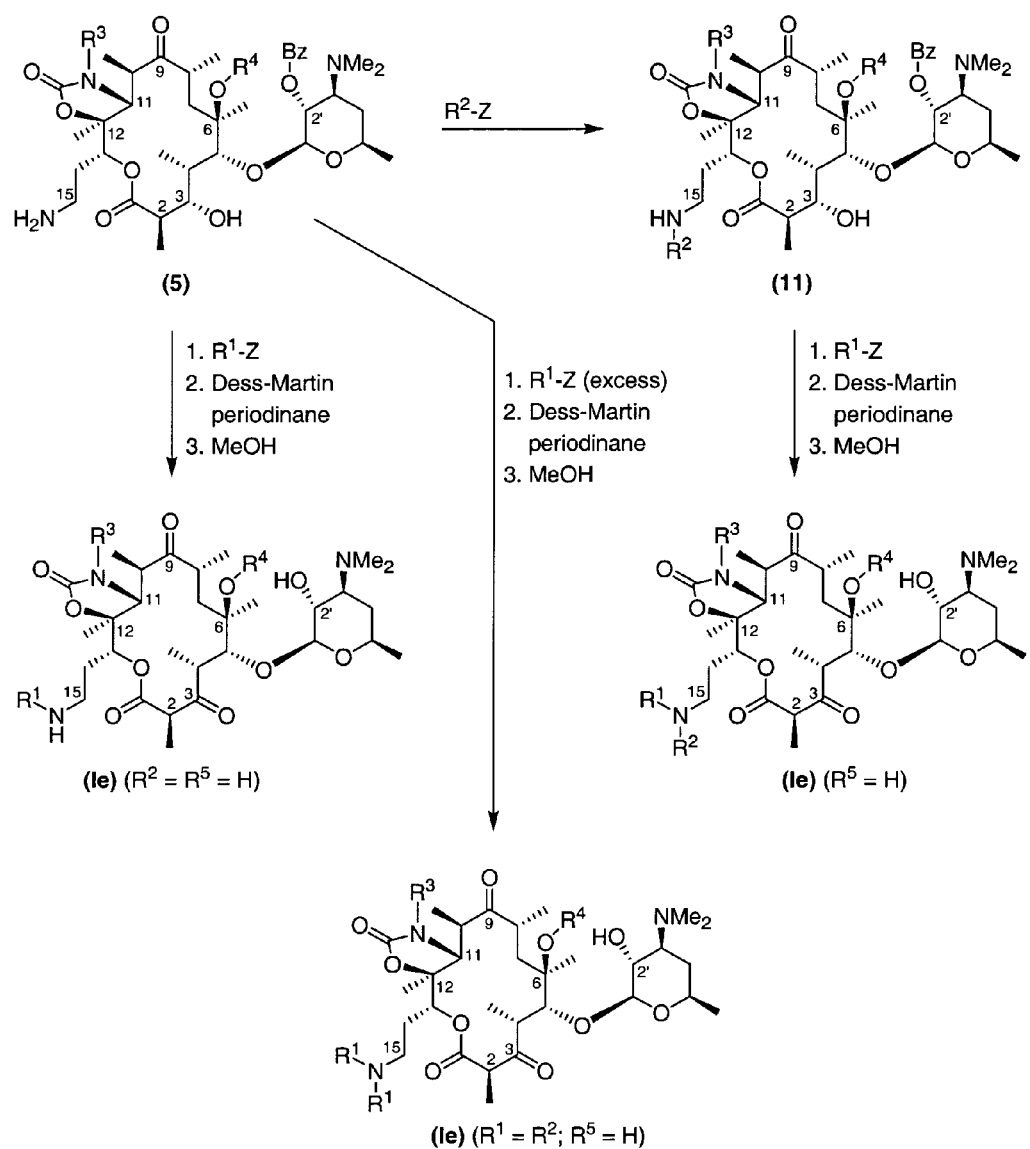

FIG. 5 shows schemes for making compounds represented by formula Ie. Monoalkylation with a halide or other alkylating agent $R^2Z$ produces intermediate amine 11. A second alkylation with an alkyl halide or other alkylating agent $R^1Z$, Dess-Martin oxidation, and 2'-benzoyl removal then produces compound Ie where $R^5$ is H and $R^2$ is other than H but different from $R^1$. Direct alkylation of amine 5 with a limited amount of $R^1Z$ produces, after oxidation and methanolysis, compound Ie where $R^2$ and $R^5$ are both H. Lastly, alkylation with an excess of $R^1Z$ produces, after oxidation and methanolysis, compounds Ie where $R^1$ and $R^2$ are the same and $R^5$ is H. In each instance, further elaboration of the initially obtained compounds Ie by fluorination with N-fluorobenzenesulfonimide produces the embodiment in which $R^5$ if F. Those skilled in the art will appreciate that, in practice, it is often difficult to stop an alkylation at the monoamine stage.

Figure 6:
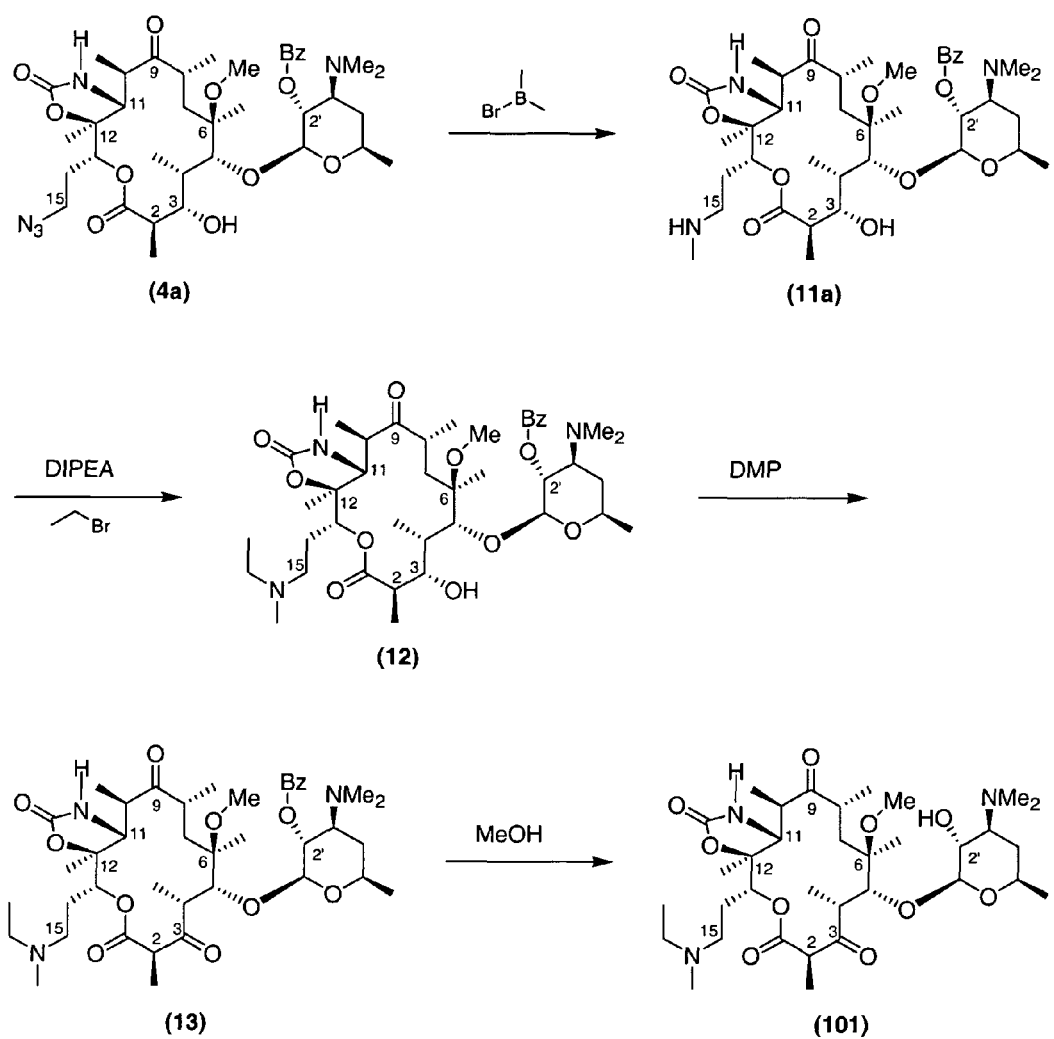

FIG. 6 shows an alternative scheme for making compounds of represented by formula Ie, using compound 101 as the archetype. A noteworthy feature is that the azide group of 11,12-cyclic carbamate 4a (corresponding to compound 4 of FIG. 1 in which $R^3$ is H and $R^4$ is methyl) is reduced and alkylated in a single step, yielding 15-N-methyl amine 11a (corresponding to amine 11 of FIG. 5 in which $R^3$ is H and $R^4$ is methyl).

Figure 7:
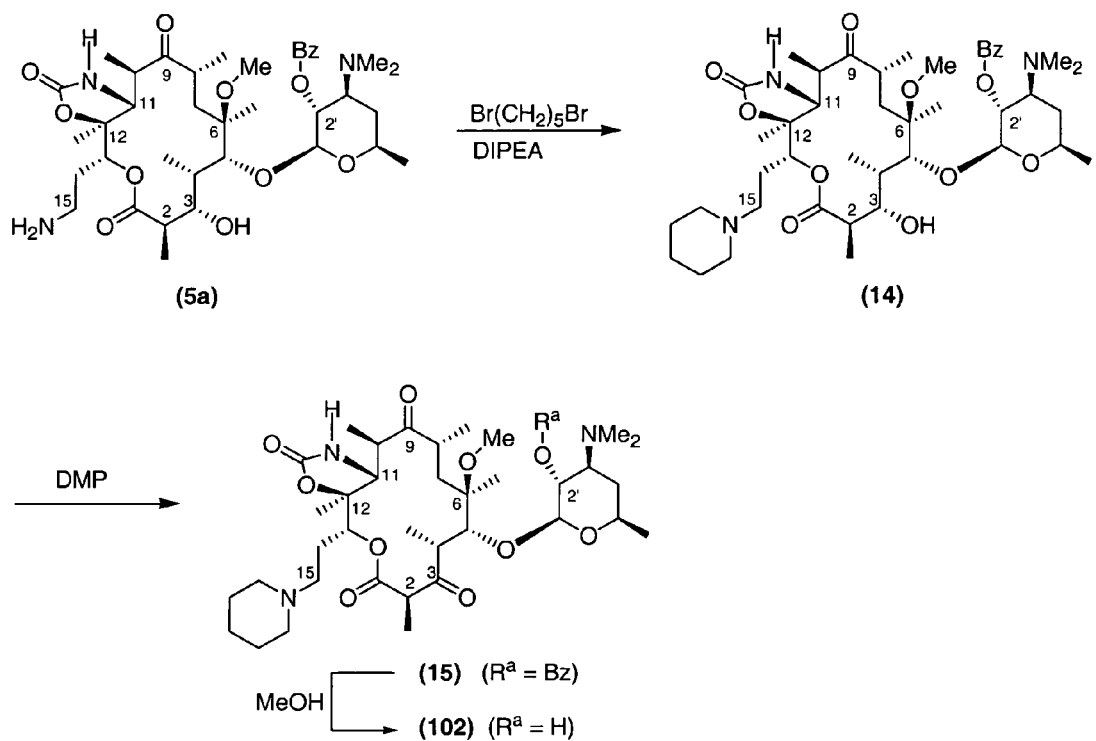

FIG. 7 shows a route for making compounds represented by formula Ie, in which $R^1$ and $R^2$ combine with the nitrogen to which they are bonded to form a heterocyclic ring structure, using compound 102 as the archetype. A noteworthy feature of this route is the use of a dihalide to bis-alkylate the 15-amino nitrogen.

Figure 8:
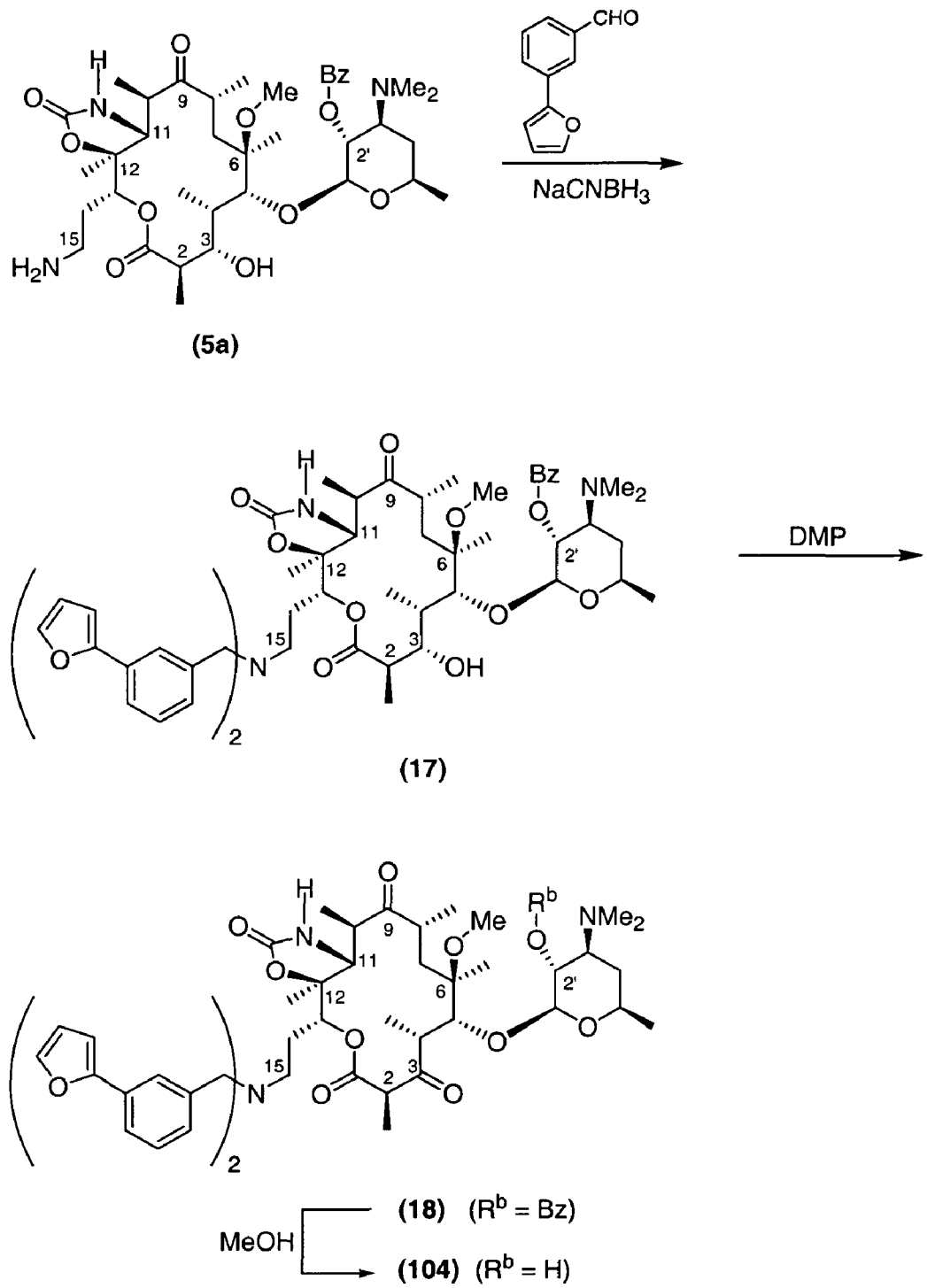

FIG. 8 shows an alternative route for making compounds represented by formula Ie, in which $R^1$ and $R^2$ are the same, using compound 104 as the archetype.

Those skilled in the art will appreciate that intermediate amines 11 of FIG. 5 and 11a of FIG. 6 can be used in the schemes of FIGS. 2, 3, and 4, in lieu of amine 5, to make compounds Ib, Ic, and Id in which $R^2$ is other than H.

Compounds of this invention may be used to treat an infection by a variety of bacterial or fungal pathogens, including *Streptococcus pneumoniae*, *Haemophilus influenzae*, *Moraxella catarrhalis*, *Bordetella* spp., *Streptococcus pyogenes*, *Chlamydia pneumoniae*, *Chlamydia psittaci*, *Chlamydia buenetti*, *Legionella pneumophila*, *Mycoplasma pneumoniae*, *Rickettsia* spp., *Franciscella tularensis*, *Bartonella* spp., *Borrelia* spp., *Leptospira* spp., *Staphylococcus epidermidis*, *Staphylococcus aureus*, *Enterococcus faecium*, *Staphylococcus haemolyticus*, *Propionibacterium* spp., *Peptostreptococcus* spp., *Clostricium difficile*, *Prevotella* spp., *Porphyromonas* spp., *Mycoplasma hominis*, *Neisseria* spp., *Bacillus anthracis*, and *Helicobacter pylori*. Compounds of this invention are especially useful for treating an infection by *Staphylococcus aureus*, *Streptococcus pneumoniae*, *Staphylococcus epidermidis*, *Enterococcus faecalis*, or *Haemophilus influenzae*.

Preferably, compounds of this invention are provided in a purified and isolated form, for example following column chromatography, high-pressure liquid chromatography, recrystallization, or other purification technique. Where particular stereoisomers of compounds of this invention are denoted, such stereoisomers preferably are substantially free of other stereoisomers.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

The composition may be in any suitable form such as solid, semisolid, or liquid form. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semisolid, or liquified form. In addition, auxiliary stabilizing, thickening, and coloring agents and perfumes may be used.

Where applicable, compounds of this invention may be formulated as microcapsules and nanoparticles. General protocols are described for example, in Bosch et al., U.S. Pat. No. 5,510,118 (1996); De Castro, U.S. Pat. No. 5,534,270 (1996); and Bagchi et al., U.S. Pat. No. 5,662,883 (1997), which are all incorporated herein by reference. By increasing the ratio of surface area to volume, these formulations allow for the oral delivery of compounds that would not otherwise be amenable to oral delivery.

Dosage levels of the compounds of the present invention are of the order from about 0.1 mg to about 100 mg per kilogram of body weight per day, preferably from about 1 mg to about 50 mg per kilogram of body weight per day. More preferably, the dosage levels are from about 5 mg to about 20 mg per kilogram of body weight per day, corresponding to 350 mg to 1400 mg per patient per day, assuming a 70 kg patient. In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain carrier material, which may vary from about 5 percent to about 95 percent of the total composition. Dosage unit forms will generally contain from about 5 mg to about 500 mg of active ingredient.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

The practice of this invention can be further understood by reference to the following examples, which are provided by way of illustration and not of limitation.

Example 1

Compound 101

Reference is made to FIG. 6, which summarizes the synthesis of compound 101.

Compound 11a. A solution of 11,12-cyclic carbamate 4a in 1,2-dichloroethane was treated under nitrogen with excess bromodimethylborane (see Dorow et al., *J. Org. Chem.* 60, 4986-4987 (1995), incorporated herein by reference) at 25° C. The reaction mixture was stirred at ambient temperature for 1 hour and was taken up in saturated aqueous sodium bicarbonate. The mixture was extracted with dichloromethane ("DCM"). The combined organic phases were dried with sodium sulfate and concentrated under reduced pressure. The resultant compound 11a was obtained as white solid, which was pure by MS, $^1$H-NMR, and thin layer chromatography ("TLC"). It was used for subsequent reactions without further purification. MS calculated for $C_{39}H_{62}N_3O_{11}$ (M+1) 748.4. Found 748.2.

Compound 12. A solution of compound 11a, ethyl bromide (1.3 eq), and N-ethyldiisopropylamine ("DIPEA", 2.0 eq) in acetonitrile was stirred at 65° C. overnight. The reaction mixture was taken up in saturated aqueous sodium bicarbonate The mixture was extracted with DCM. The organic phases were combined, dried with sodium sulfate, and concentrated under reduced pressure. The crude compound 12 was purified by column chromatography (5% methanol/DCM).

3-Keto Intermediate 13. A solution compound 12 in DCM was treated with Dess-Martin periodinane ("DMP," 4 eq; see Nicolaou et al., *J. Am. Chem. Soc.* 124 (10), 2212-2220 (2002), incorporated herein by reference) at 0° C. for 30 min. The reaction mixture was taken up in saturated aqueous sodium bicarbonate. The mixture was extracted with DCM. The organic phases were combined, dried with sodium sulfate, and concentrated under reduced pressure. The crude 3-keto intermediate 13 was purified by column chromatography (5% methanol/DCM). MS calculated for $C_{41}H_{64}N_3O_{11}$ (M+1) 774.4. Found 774.2.

Compound 101. A solution of 3-keto intermediate 13 in methanol was stirred at 70° C. overnight. The volatiles were removed under reduced pressure. The crude compound 101 was purified by column chromatography (10% methanol/DCM). MS calculated for $C_{34}H_{60}N_3O_{10}$ (M+1) 670.4. Found 670.0.

Example 2

Compound 102

Reference is made to FIG. 7, which summarizes the synthesis of compound 102.

Compound 14. A solution of amine 5a, 1,5-dibromopentane (0.5 eq), and DIPEA (2.0 eq) in acetonitrile was stirred at 70° C. over night. The reaction mixture was taken up in saturated aqueous sodium bicarbonate. The mixture was extracted with DCM. The organic phases were combined, dried with sodium sulfate, and concentrated under reduced pressure. The crude compound 14 was purified by column chromatography (5% methanol/DCM). MS calculated for $C_{43}H_{68}N_3O_{11}$ (M+1) 802.5. Found 802.4.

3-Keto Intermediate 15. A solution of compound 14 in DCM was treated with DMP (4 eq) at 0° C. for 30 min. The reaction mixture was taken up in saturated aqueous sodium bicarbonate. The mixture was extracted with DCM. The organic phases were combined, dried with sodium sulfate, and concentrated under reduced pressure. The crude 3-keto intermediate 15 was purified by column chromatography (5% methanol/DCM).

Compound 102. A solution of 3-keto intermediate 15 in methanol was stirred at 70° C. overnight. The volatiles were removed under reduced pressure. The resultant crude compound 102 was purified by column chromatography (5~10% methanol/DCM). MS calculated for $C_{36}H_{62}N_3O_{10}$ (M+1) 696.4. Found 696.5.

Example 3

Compound 103

Compound 103 was made generally according to FIG. 5, via intermediate 16.

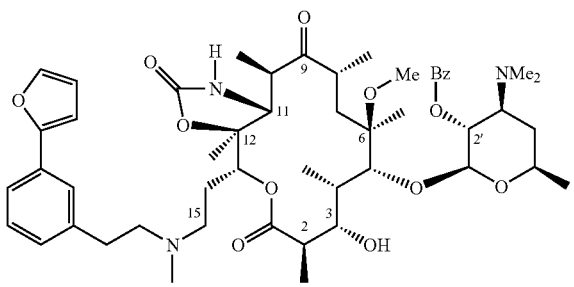

(16)

Compound 16. 3-(2-Furyl)phenethyl bromide was prepared as follows: A reaction mixture of 2-(3-bromo-phenyl)-ethanol (1.0 eq.), furan-2-boranic acid (1.1 eq), 2N aqueous sodium carbonate, and tetrakis(triphenylphosphine)palladium(0) ("TTPP" or "(PPh$_3$)$_4$Pd") (0.1 eq) in toluene was stirred under nitrogen at 80° C. overnight. The mixture was diluted with ethyl acetate, washed with water and brine, dried over sodium sulfate, and concentrated. Purification by column chromatography (5-10% ethyl acetate/hexanes) gave 2-(3-furan-2-yl-phenyl)ethanol.

A solution of 2-(3-furan-2-yl-phenyl)ethanol and carbon tetrabromide in DCM was treated with triphenylphosphine at 0° C. The resultant mixture was stirred at room temperature for one hr. The volatiles were removed under reduced pressure. Purification by column chromatography (5% ethyl acetate/hexanes) gave 3-(2-furyl)phenethyl bromide. $^1$H NMR (CDCl$_3$) δ 7.57 (d, J=1.6, 1H), 7.55 (s, 1H), 7.47 (s, 1H), 7.33 (t, J=8.0 Hz, 1H), 7.11 (d, J=8.0 Hz, 1H), 6.66 (m, 1H), 6.47 (m, 1H), 3.60 (t, J=7.2 Hz, 2H), 3.20 (t, J=7.2 Hz, 2H).

A solution of compound 11a (Example 1), 3-(2-furyl)phenethyl bromide (2.0 eq), and DIPEA (4.0 eq) in acetonitrile was stirred at 65° C. overnight. The reaction mixture was taken up in saturated aqueous sodium bicarbonate. The mixture was extracted with DCM. The organic phases were combined, dried with sodium sulfate, and concentrated under reduced pressure. The crude compound 16 was purified by column chromatography (5% methanol/DCM). MS calculated for $C_{51}H_{72}N_3O_{12}$ (M+1) 918.5. Found 918.1.

Compound 103. Compound 16 was converted to compound 103 by a two-step sequence, generally following the procedure of FIG. 2. First, a solution of compound 16 in DCM was treated with DMP (4 eq) at 0° C. for 30 min. The reaction mixture was taken up in saturated aqueous sodium bicarbonate. The mixture was extracted with DCM. The organic phases were combined, dried with sodium sulfate, and concentrated under reduced pressure. Purification by column chromatography (5% methanol/DCM) gave the intermediate 3-keto product. MS calculated for $C_{51}H_{70}N_3O_{12}$ (M+1) 916.5. Found 916.0.

Next, removal of the 2'-benzoyl group was effected by methanolysis as follows: A solution of the 3-keto intermediate in methanol was stirred at 70° C. overnight. The volatiles were removed under reduced pressure. The resultant crude compound 103 was purified by column chromatography (50% acetone/hexanes, 1% triethylamine). MS calculated for $C_{44}H_{66}N_3O_{11}$ (M+1) 812.4. Found 812.2.

Example 4

Compound 104

Reference is made to FIG. 8, which summarizes the synthesis of compound 104.

Dialkylated Compound 17. A solution of amine 5a, 3-furan-2-yl-benzaldehyde (commerically available, 1.0 eq), and acetic acid in methanol was stirred at room temperature for 2 hours before sodium cyanoborohydride was added. The reaction mixture was stirred at ambient temperature for 1 hr before being quenched by the addition of water. The resultant mixture was extracted with DCM. The combined organic phases were dried and concentrated. Purification by column chromatography gave the desired compound 17. MS calculated for $C_{60}H_{76}N_3O_{13}$ (M+1) 1046.5. Found 1046.0.

3-Keto Intermediate 18. A solution of dialkylated compound 17 in DCM was treated with DMP (4 eq) at 0° C. for 30 min. The reaction mixture was taken up in saturated aqueous sodium bicarbonate. The mixture was extracted with DCM. The organic phase was combined, dried with sodium sulfate, and concentrated under reduced pressure. The crude 3-keto intermediate 18 was purified by column chromatography (5% methanol/DCM).

Compound 104. A solution of 3-keto intermediate 18 in methanol was stirred at 70° C. overnight. The volatiles were removed under reduced pressure. Purification by column chromatography (5% methanol/DCM) gave compound 104. MS calculated for $C_{53}H_{69}N_3O_{12}$ (M+1) 940.5. Found 940.3.

Example 5

Compounds 105, 106, and 107

Compounds 105, 106, and 107 were prepared according to the scheme shown in FIG. 2 and the general procedure given below, using commercially available sulfonyl chlorides.

General procedure. The hydrochloride salt of compound 5a (1 eq) was dissolved in 1 mL of DCM, followed by addition of triethylamine (3 eq) and the desired sulfonyl chloride (1.2 eq) at room temperature. The reaction was then allowed to proceed for two hours at room temperature, or until TLC analysis showed no starting material remaining. The resulting solution was diluted with 20 mL of saturated aqueous sodium bicarbonate and stirred for 30 min before it was extracted with 50 mL of ethyl acetate. The ethyl acetate extract was washed with 20 mL of water, and 20 mL of brine, before it was dried over magnesium sulfate. The solvent was evaporated under vacuum and the residue was purified by flash column chromatography to provide the 2'-O-benzoyl-3-hydroxy sulfonamide intermediate 6 (FIG. 2) as a white powder.

To a solution of intermediate 6 in 2 mL of DCM was added an excess of sodium bicarbonate and DMP (4 eq) as a solid. The resultant mixture was stirred at ambient temperature for 30 min. Then the mixture was treated with 15 mL of 5% sodium thiosulfate aqueous solution for 10 min before it was diluted with saturated sodium bicarbonate and extracted with 40 mL of DCM. The organic extract was washed sequentially with saturated sodium bicarbonate, water, and brine. The organic phase was dried over magnesium sulfate, filtered, and evaporated to give the 2'-O-benzoyl-3-keto sulfonamide intermediate 7 (FIG. 2) as a slightly yellow solid, which was used for next step without further purification.

Intermediate 7 was dissolved in 2 mL of methanol. The solution was heated at 70° C. with stirring overnight. Evaporation of methanol under vacuum gave a yellow solid, which was purified by flash column chromatography to provide a compound of structure Ib (FIG. 2). The overall yield of above reactions was about 50%, depending on the side chain.

Compound 105. MS: $[M+H]^+$=819.3578 (calculated 819.3772). $^{13}$C NMR (CDCl$_3$, 100 MHz) δ 218.0, 204.1, 169.3, 157.4, 151.4, 143.0, 137.0, 135.5, 133.4, 130.8, 128.7, 125.5, 122.2, 103.7, 82.9, 79.2, 77.9, 73.2, 70.2, 69.5, 65.7, 57.6, 50.9, 49.1, 48.0, 44.4, 40.4, 40.1, 39.7, 37.3, 30.8, 29.8, 28.1, 21.1, 19.3, 17.5, 16.3, 14.2, 13.5, 13.2.

Compound 106. MS: $[M+H]^+$=818.3609 (calculated 818.3819). $^{13}$C NMR (CDCl$_3$, 100 MHz) δ 217.9, 203.8, 169.5, 157.4, 134.4, 134.2, 129.3, 129.0, 128.9, 128.3, 128.0, 126.8, 124.3, 124.0, 103.7, 82.8, 79.2, 77.9, 73.1, 70.2, 69.5, 65.7, 57.8, 50.8, 49.2, 48.1, 44.3, 40.1, 40.0, 39.7, 37.3, 29.7, 29.2, 28.1, 21.1, 19.3, 17.5, 16.4, 14.2, 13.5, 13.2.

Compound 107. MS: [M+H]+=818.3571(calculated 818.3819). $^{13}$C NMR (CDCl$_3$, 100 MHz) δ 217.9, 203.8, 169.6, 157.4, 136.4, 134.7, 132.0, 129.6, 129.2, 128.6, 128.3, 127.8, 127.4, 122.2, 103.8, 82.9, 79.3, 77.9, 73.2, 70.2, 69.5, 65.7, 57.8, 50.9, 49.2, 48.1, 44.4, 40.1, 39.9, 39.7, 37.3, 30.8, 29.7, 29.2, 28.1, 21.1, 19.3, 17.5, 16.5, 14.2, 13.5, 13.2

Example 6

Compound 108

Figure 9:
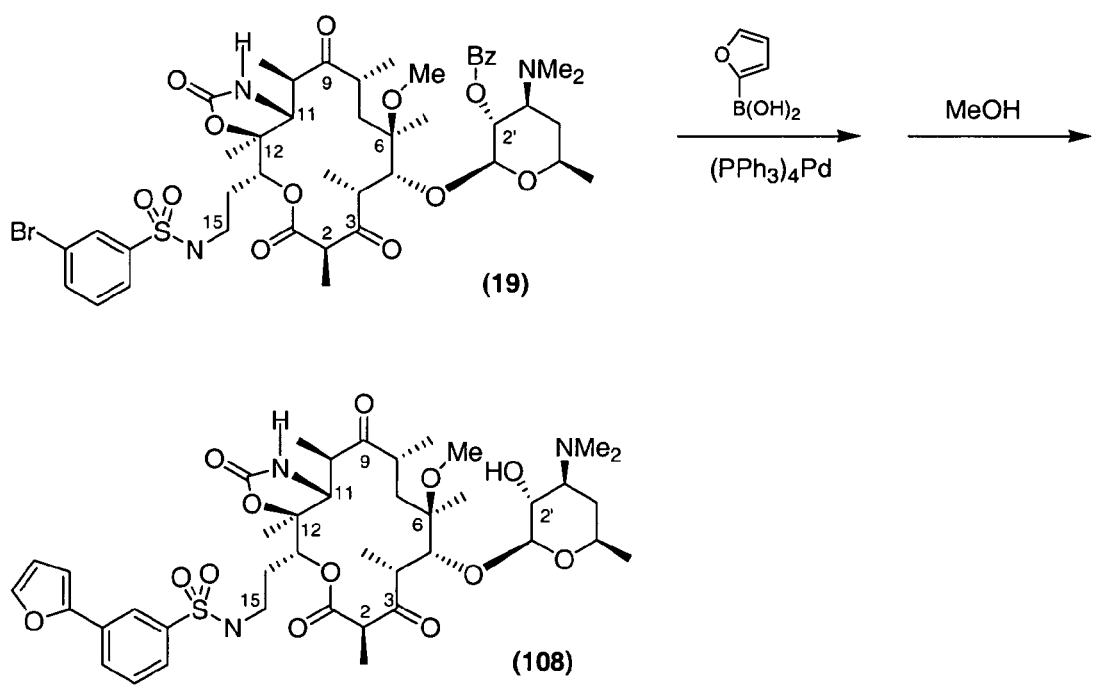

Compound 19 was prepared following the scheme of FIG. 2 and converted to compound 108 as shown in FIG. 9:

Compound 19. A solution of amine 5a and DIPEA (3.0 eq) in DCM was treated with 3-bromobenzenesulfonyl chloride (1.1 eq) at room temperature for one hr. The reaction was diluted with saturated aqueous sodium bicarbonate. The resultant mixture was extracted with DCM. The combined organic phases were dried over sodium sulfate and concentrated. The crude intermediate 3-hydroxy compound was purified by column chromatography (2% methanol/DCM). MS calculated for $C_{44}H_{63}BrN_3O_{13}S$ (M+1) 952.3. Found 951.9.

A solution of the intermediate 3-hydroxy compound in DCM was treated with DMP (4 eq) at 0° C. for 30 min. The reaction mixture was taken up in saturated aqueous sodium bicarbonate. The mixture was extracted with DCM. The organic phases were combined, dried with sodium sulfate and concentrated under reduced pressure. The crude compound 18 was purified by column chromatography (2% methanol/DCM).

Compound 108. A mixture of compound 19, 2-furanboranic acid (commercially available, 2.0 eq), TTPP (0.1 eq.), and sodium carbonate (2N, 2.0 eq) in DMF was stirred under nitrogen at 85° C. overnight. The mixture was diluted with ethyl acetate. The organic phase was washed with water and brine, dried, and concentrated. The crude product was dissolved in methanol and the mixture was heated at 70° C. overnight. The volatiles were removed under reduced pressure. Purification by column chromatography (2% methanol/DCM) gave compound 108. MS calculated for $C_{41}H_{60}N_3O_{13}S$ (M+1) 834.3. Found 833.8.

Example 7

Compound 109

Compound 109 was prepared generally following the procedure laid out in FIG. 3.

3-Pyridin-3-yl-phenol. A mixture of 3-bromopyridine, 3-methoxyphenylboronic acid (1.3 eq.), 2N sodium carbonate, and (PPh$_3$)$_4$Pd in toluene was stirred at 80° C. over night. The reaction mixture was taken up in ethyl acetate. The organic phase was washed with saturated sodium bicarbonate and then brine, dried, and concentrated. The residue was diluted in CDM and the solution was treated with boron tribromide at −78° C. (acetone-dry ice bath). The bath was allowed to warm up to room temperature over approximately 5 hr. Methanol was added to quench the reaction. The volatiles were removed under reduced pressure. The residue was taken up in ethyl acetate and the resultant solution was washed with saturated sodium bicarbonate. The organic phase was then extracted with 3 N hydrochloric acid, which was then basified with sodium bicarbonate The aqueous phase was extracted with ethyl acetate, which was washed with saturated brine, dried, and concentrated. The resultant white solid was pure by TLC, MS, and $^1$H-NMR and was used without further purification.

3-Pyridin-3-yl-phenyl chloroformate. A solution of 3-pyridin-3-yl-phenol in tetrahydrofuran was treated with 20% phosgene in toluene (1.0 eq.) at 25° C. The reaction mixture was then treated with N,N-dimethylaniline (1.3 eq) at 0° C. The reaction mixture was stirred at 25° C. over night. The volatiles were removed under reduced pressure. The crude product 3-pyridin-3-yl-phenyl chloroformate was used without further purification.

2'-O-Benzoyl-3-hydroxy intermediate. A solution of amine 5a in DCM was treated with DIPEA (2.5 eq) followed by 3-pyridin-3-yl-phenyl chloroformate (1.05 eq) at 0° C. The reaction mixture was stirred at 0° C. for 30 min and was taken up in saturated aqueous sodium bicarbonate. The mixture was extracted with DCM. The organic phases were combined, dried with sodium sulfate and concentrated under reduced pressure. The crude 2'-O-benzoyl-3-hydroxy intermediate (corresponding to formula 8 in FIG. 3) was purified by column chromatography (5% MeOH/CH$_2$Cl$_2$). MS calculated for $C_{50}H_{67}N_4O_{13}$ (M+1) 931.4. Found 931.3.

2'-O-Benzoyl-3-keto intermediate. A solution of the 2'-O-benzoyl-3-hydroxy intermediate in DCM was treated with DMP (4 eq) at 0° C. for 30 min. The reaction mixture was taken up in saturated aqueous sodium bicarbonate. The mixture was extracted with DCM. The organic phases were combined, dried with sodium sulfate, and concentrated under reduced pressure. The crude 2'-O-benzoyl-3-keto intermediate was purified by column chromatography (5% methanol/DCM). MS calculated for $C_{50}H_{65}N_4O_{13}$ (M+1) 929.4. Found 929.3.

Compound 109. A solution of the 2'-O-benzoyl-3-keto intermediate in methanol was stirred at 70° C. for 2 hr. The volatiles were removed under reduced pressure. The resultant crude product was purified by column chromatography (5% methanol/DCM) to give the compound 109. MS calculated for $C_{43}H_{61}N_4O_{12}$ (M+1) 825.4. Found 825.3.

Example 8

Compound 110

Compound 110 was prepared with 4-pyridin-3-yl-phenyl chloroformate using a reaction sequence analogous to that in Example 7. MS calculated for $C_{43}H_{61}N_4O_{12}$ (M+1) 825.4. Found 825.4. (4-Pyridin-3-yl-phenyl chloroformate was prepared by following analogously the procedure in Example 7, using 4-bromopyridine.)

Example 9

Compound 111

Compound 111 was prepared with biphenyl-3-chloroformate using a reaction sequence analogous to that in Example 7. MS calculated for $C_{44}H_{62}N_3O_{12}$ (M+1) 824.4. Found 824.4. (Biphenyl-3-chloroformate was prepared by following analogously the procedure in Example 7, using 3-phenylphenol.)

Example 10

Compound 112

Compound 112 was prepared with biphenyl-4-chloroformate using a reaction sequence analogous to that in Example 7. MS calculated for $C_{44}H_{62}N_3O_{12}$ (M+1) 824.4. Found 824.5. (Biphenyl-4-chloroformate was prepared by following analogously the procedure in Example 7, using 4-phenylphenol.)

Example 11

Compound 113

Compound 113 was prepared with commercially available naphthalen-2-chloroformate using a reaction sequence analogous to that in Example 7. MS calculated for $C_{42}H_{60}N_3O_{12}$ (M+1) 798.4. Found 798.4.

Example 12

Compounds 114 and 118

Compound 114 was prepared with commercially available naphthalen-1-chloroformate using a reaction sequence analogous to that in Example 7. During the methanolysis step, some alkoxy exchange occurred and compound 118 was isolated in addition to compound 114.

Compound 114. MS calculated for $C_{42}H_{60}N_3O_{12}$ (M+1) 798.4. Found 798.8.

Compound 118. MS calculated for $C_{33}H_{56}N_3O_{12}$ (M+1) 686.4. Found 686.0.

Example 13

Compound 115

Compound 115 was prepared with commercially available 9-fluorenyl-methoxycarbonyl chloride using a reaction sequence analogous to that in Example 7. MS calculated for $C_{46}H_{64}N_3O_{12}$ (M+1) 850.4. Found 850.3.

Example 14

Compound 116

Compound 116 was prepared with commercially available 4-fluorophenyl chloroformate using a reaction sequence analogous to that in Example 7. MS calculated for $C_{38}H_{57}FN_3O_{12}$ (M+1) 766.4. Found 766.4.

Example 15

Compound 117

Compound 117 was prepared with commercially available isobutyl chloroformate using a reaction sequence analogous to that in Example 7. MS calculated for $C_{26}H_{62}N_3O_{12}$ (M+1) 728.4. Found 728.5.

Example 16

Compound 119

Compound 119 was prepared following the synthetic scheme laid out in FIG. 4, proceeding via an intermediate corresponding to structure 9.

A solution of amine 5a and DIPEA (2.0 eq) in DCM was treated with 1-naphthylisocyanate (commercially available, 1.0 eq) at room temperature. The reaction mixture was stirred at room temperature for 30 min, taken up in saturated aqueous sodium bicarbonate, and extracted with DCM. The organic phases were combined, dried with sodium sulfate, and concentrated under reduced pressure. The crude 2'-O-benzoyl-3'-hydroxy intermediate corresponding to structure 9 was purified by column chromatography (5% methanol/DCM).

A solution of the 2'-O-benzoyl-3'-hydroxy intermediate in DCM was treated with pyridinium dichromate (2.0 eq) at room temperature for 6 hours. The mixture was taken up in saturated aqueous sodium bicarbonate and DCM. The mixture was washed with water and brine. The organic phase was dried with sodium sulfate and concentrated under reduced pressure. The crude 2'-O-benzoyl-3-keto intermediate was purified by column chromatography (5% methanol/DCM).

A solution of the 2'-benzoyl-3-keto intermediate in methanol was stirred at 70° C. overnight. The volatiles were removed under reduced pressure. The resultant crude compound 119 was purified by column chromatography (5% methanol/DCM). MS calculated for $C_{42}H_{61}N_4O_{11}$ (M+1) 797.4. Found 797.1.

Example 17

Biological Activity

Using a microdilution assay procedure, compounds of this invention were found to be active against a variety of bacteria, in particular *Staphylococcus aureus, Streptococcus pneumoniae, Staphylococcus epidermidis, Enterococcus faecalis,* and/or *Haemophilus influenzae*. Minimum inhibitory concentrations (MICs) are presented in Table B, along with comparative data for erythromycin A and telithromycin.

TABLE B

| | Compound (MIC, µg/mL) | | | | | | |
|---|---|---|---|---|---|---|---|
| Microorganism | Ery A | Tel | 101 | 102 | 103 | 104 | 105 |
| *S. aureus* | | | | | | | |
| ATCC 6538p | 0.098 | 0.025 | 6.25 | ND | 0.098 | >12.5 | 0.049 |
| ATCC 14154 | >12.5 | >12.5 | 6.25 | ND | 0.39 | 6.25 | 0.39 |
| ATCC 29213 | 0.20 | 0.025 | 6.25 | ND | 0.39 | 6.25 | 0.049 |

TABLE B-continued

| Microorganism | | | | | | | |
|---|---|---|---|---|---|---|---|
| *S. pneumoniae* | | | | | | | |
| ATCC 6301 | 0.025 | 0.025 | 0.2 | 0.098 | 0.049 | 3.12 | 0.01 |
| ATCC 700671 | 0.049 | 0.025 | 0.39 | 3.12 | 0.049 | 3.12 | 0.01 |
| ATCC 700676 | 6.25 | 0.098 | 6.25 | 0.78 | 0.049 | 6.25 | 0.01 |
| ATCC 700677 | 6.25 | 0.025 | >12.5 | >12.5 | 0.098 | 6.25 | 0.01 |
| ATCC 700905 | 3.12 | 0.025 | 3.12 | 0.098 | 0.049 | >12.5 | 0.01 |
| ATCC 700906 | >12.5 | 0.20 | >12.5 | >12.5 | >12.5 | >12.5 | 0.39 |
| ATCC 49619 | 0.049 | 0.049 | 0.78 | 0.2 | 0.049 | >12.5 | 0.01 |
| *S. epidermidis* | | | | | | | |
| ATCC 12228 | 0.20 | 0.025 | 6.25 | ND | 0.049 | 6.25 | 0.025 |
| *E. faecalis* | | | | | | | |
| ATCC 51575 | >12.5 | >12.5 | 6.25 | ND | 12.5 | 12.5 | 0.025 |
| *H. influenzae* | | | | | | | |
| ATCC 9006 | 1.56 | 1.56 | >12.5 | 3.12 | >12.5 | >12.5 | 3.12 |
| ATCC 49766 | 6.25 | 3.12 | >12.5 | 6.25 | >12.5 | >12.5 | 6.25 |

| | Compound (MIC, µg/mL) | | | | | | |
|---|---|---|---|---|---|---|---|
| Microorganism | 106 | 107 | 108 | 109 | 110 | 111 | 112 |
| *S. aureus* | | | | | | | |
| ATCC 6538p | 0.01 | 0.01 | 0.025 | ND | ND | ND | ND |
| ATCC 14154 | 3.12 | 1.56 | 0.049 | ND | ND | ND | ND |
| ATCC 29213 | 0.025 | 0.025 | 0.025 | ND | ND | ND | ND |
| *S. pneumoniae* | | | | | | | |
| ATCC 6301 | 0.01 | 0.01 | 0.025 | 0.025 | 0.025 | 0.025 | 0.025 |
| ATCC 700671 | 0.01 | 0.01 | 0.025 | 0.025 | 0.025 | 0.025 | 0.025 |
| ATCC 700676 | 0.01 | 0.01 | 0.025 | 0.025 | 0.025 | 0.025 | 0.025 |
| ATCC 700677 | 0.01 | 0.01 | 0.025 | 0.025 | 0.025 | 0.025 | 0.78 |
| ATCC 700905 | 0.01 | 0.01 | 0.025 | 0.025 | 0.025 | 0.025 | 0.025 |
| ATCC 700906 | 12.5 | 3.12 | 0.049 | 0.025 | 0.049 | 0.025 | 0.049 |
| ATCC 49619 | 0.01 | 0.01 | 0.025 | 0.025 | 0.025 | 0.049 | 0.049 |
| *S. epidermidis* | | | | | | | |
| ATCC 12228 | 0.025 | 0.025 | 0.025 | ND | ND | ND | ND |
| *E. faecalis* | | | | | | | |
| ATCC 51575 | 0.025 | 0.025 | 0.025 | ND | ND | ND | ND |
| *H. influenzae* | | | | | | | |
| ATCC 9006 | 6.25 | 12.5 | 12.5 | 1.56 | 1.56 | 1.56 | 3.12 |
| ATCC 49766 | 6.25 | 12.5 | >12.5 | 1.56 | 3.12 | 1.56 | 6.25 |

| | Compound (MIC, µg/mL) | | | | | | |
|---|---|---|---|---|---|---|---|
| Microorganism | 113 | 114 | 115 | 116 | 117 | 118 | 119 |
| *S. aureus* | | | | | | | |
| ATCC 6538p | ND | 0.025 | ND | ND | ND | 0.49 | ND |
| ATCC 14154 | ND | 0.025 | ND | ND | ND | 0.39 | ND |
| ATCC 29213 | ND | ND | ND | ND | ND | ND | ND |
| *S. pneumoniae* | | | | | | | |
| ATCC 6301 | 0.025 | 0.025 | 0.025 | 0.025 | 0.025 | 0.025 | 0.025 |
| ATCC 700671 | 0.025 | 0.025 | 0.025 | 0.025 | 0.098 | 0.049 | 0.049 |
| ATCC 700676 | 0.025 | 0.098 | 0.025 | 0.025 | 0.025 | 0.098 | 0.049 |
| ATCC 700677 | 0.025 | 0.049 | 0.025 | 0.39 | >12.5 | 0.39 | 0.78 |
| ATCC 700905 | 0.025 | 0.025 | 0.025 | 0.025 | 0.025 | 0.98 | 0.025 |
| ATCC 700906 | 0.025 | 6.25 | 0.025 | 0.098 | >12.5 | >12.5 | 0.098 |
| ATCC 49619 | 0.025 | 0.049 | 0.025 | 0.049 | 0.025 | 0.049 | 0.025 |
| *S. epidermidis* | | | | | | | |
| ATCC 12228 | ND | ND | ND | ND | ND | ND | ND |

TABLE B-continued

| E. faecalis | | | | | | | |
|---|---|---|---|---|---|---|---|
| ATCC 51575 | ND | ND | ND | ND | ND | ND | ND |
| H. influenzae | | | | | | | |
| ATCC 9006 | 1.56 | 6.25 | 0.78 | 3.12 | 6.25 | 6.25 | 6.25 |
| ATCC 49766 | 1.56 | 3.12 | 1.56 | 6.25 | 6.25 | 3.12 | 3.12 |

Ery A = erythromycin A (comparative)
Tel = telithromycin (comparative)
ND = No data In Table B, in some instances multiple assays were performed for a compound/strain combination, in which case the reported MIC is the average. S. pneumoniae ATCC 6301, ATCC 700671, and ATCC 49619 and S. aureus ATCC 6538p and ATCC 29213 are erythromycin sensitive strains. Conversely, S. pneumoniae ATCC 700676, ATCC 700677, ATCC 700905, and ATCC 700906 and S. aureus ATCC 14154 are erythromycin A resistant strains.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

We claim:

1. A compound having a structure according to formula I

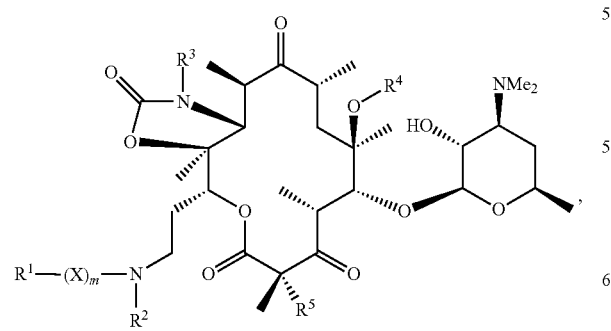

and the pharmaceutically acceptable salts and esters thereof, wherein m is 0 or 1;

X is

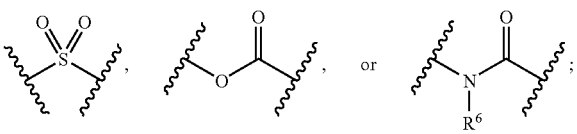

$R^1$ is $C_1$-$C_5$ alkyl, $C_2$-$C_5$ alkenyl, $C_2$-$C_5$ alkynyl, aryl, heterocyclo, (heterocyclo)alkyl, biaryl, arylalkyl, arylalkenyl, arylalkynyl, biarylalkyl, biarylalkenyl, or biarylalkynyl;

$R^2$ is H, $C_1$-$C_5$ alkyl, $C_2$-$C_5$ alkenyl, $C_2$-$C_5$ alkynyl, arylalkyl, arylalkenyl, arylalkynyl, biarylalkyl, biarylalkenyl, or biarylalkynyl; or, when m is 0, $R^1$ and $R^2$ may combine with the nitrogen to which they are commonly bonded to form a 4, 5, 6, or 7-membered heterocyclic ring structure;

$R^3$ and $R^4$ are independently H, $C_1$-$C_5$ alkyl, $C_2$-$C_5$ alkenyl, $C_2$-$C_5$ alkynyl, arylalkyl, arylalkenyl, arylalkynyl, biarylalkyl, biarylalkenyl, or biarylalkynyl;

$R^5$ is H or F; and $R^6$ is H, $C_1$-$C_5$ alkyl, $C_2$-$C_5$ alkenyl, or $C_2$-$C_5$ alkynyl, or $R^1$ and $R^6$ may combine with the nitrogen to which they are commonly bonded to form a 4, 5, 6, or 7-membered heterocyclic ring structure.

2. A compound according to claim 1, having a structure according to formula Ia

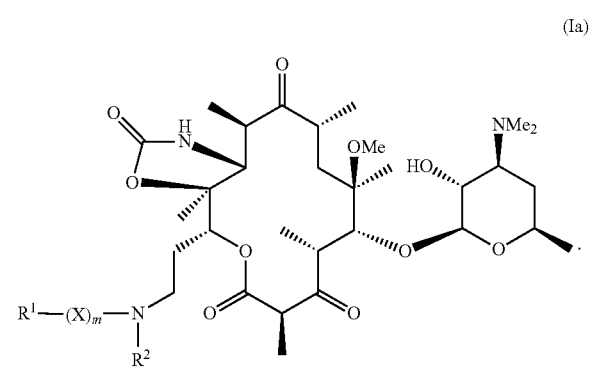

3. A compound according to claim 1, having a structure according to formula Ib

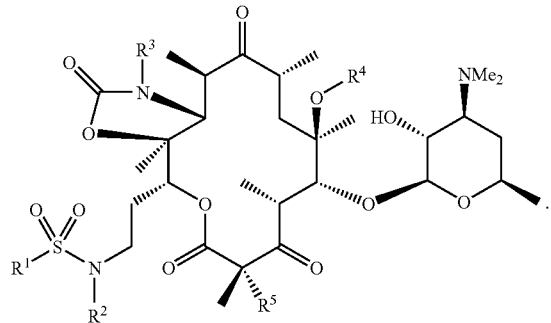
(Ib)

4. A compound according to claim 3, having a structure according to formula Ib'

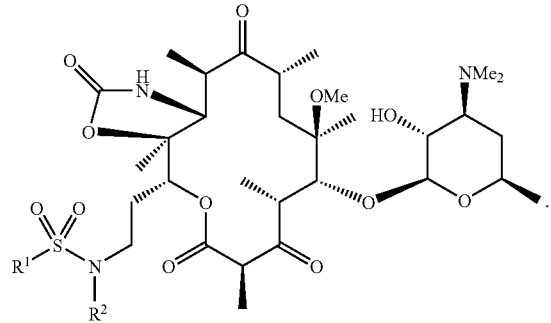
(Ib')

5. A compound according to claim 4, wherein the moiety

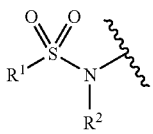

in formula Ib' is selected from the group consisting of

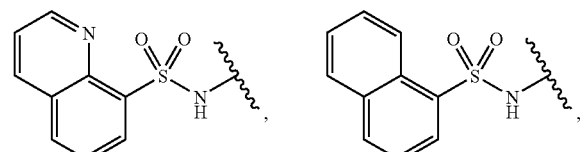

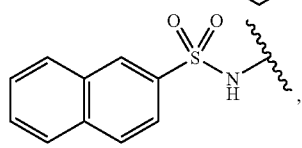

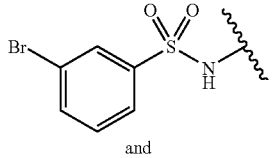
and

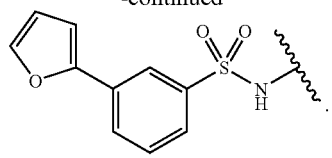

6. A compound according to claim 1, having a structure according to formula Ic

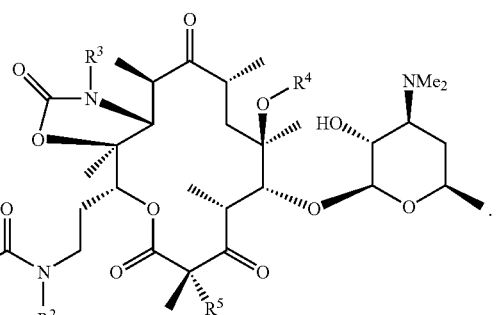
(Ic)

7. A compound according to claim 6, having a structure according to formula Ic'

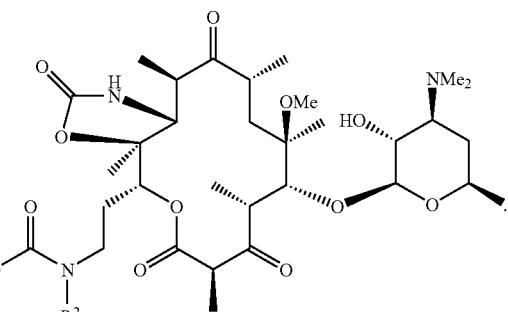
(Ic')

8. A compound according to claim 7, wherein the moiety

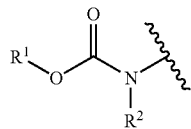

in formula Ic' is selected from the group consisting of

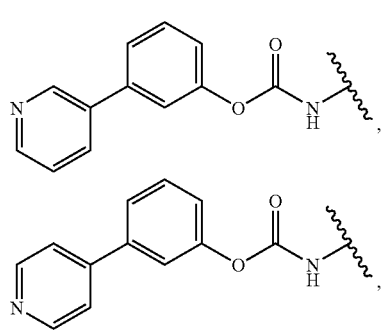

-continued
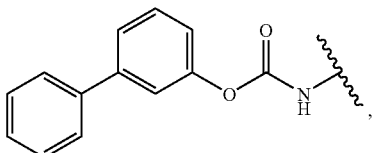
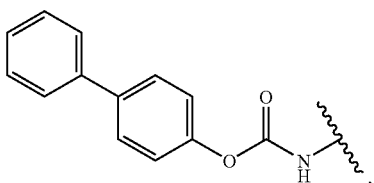
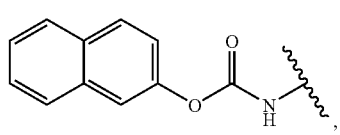
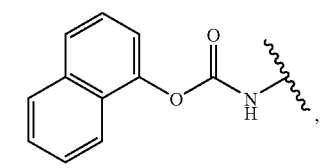
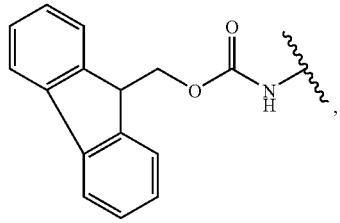
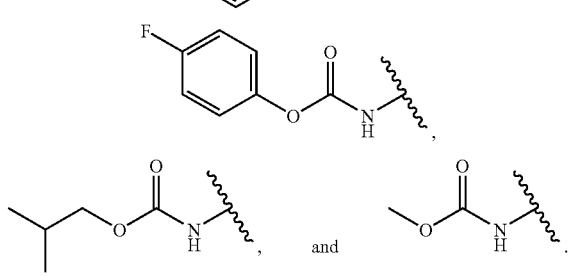
and
9. A compound according to claim 1, having a structure according to formula Id
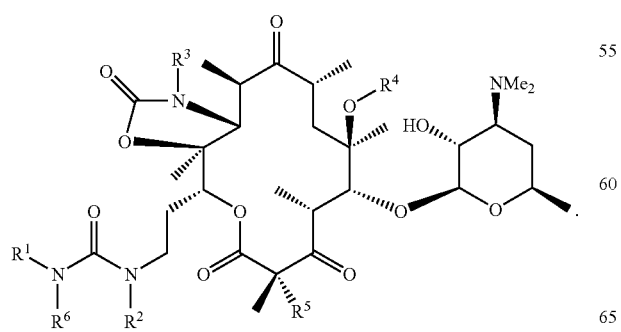
(Id)
10. A compound according to claim 9, having a structure according to formula Id'
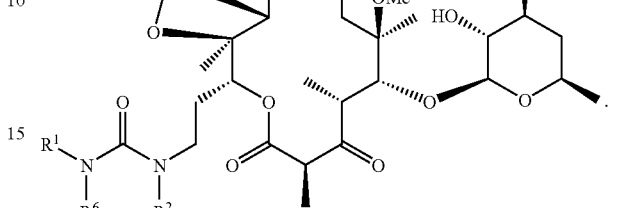
(Id')
11. A compound according to claim 10, wherein the moiety
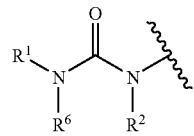
in formula Id' is
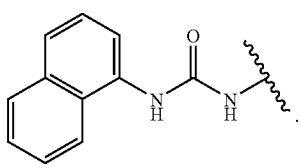
12. A compound according to claim 1, having a structure according to formula Ie
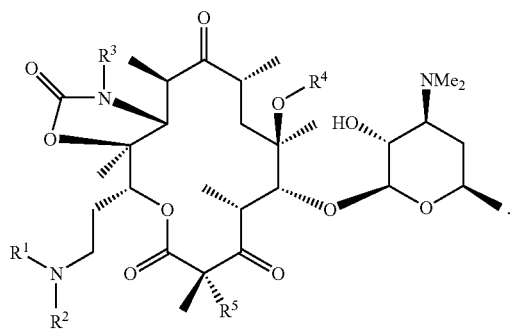
(Ie)

13. A compound according to claim 12, having a structure according to formula Ie'

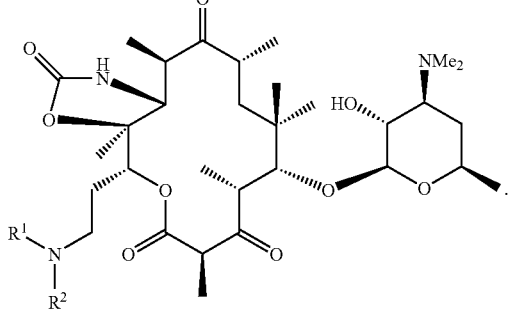

(Ie')

14. A compound according to claim 13, wherein the moiety

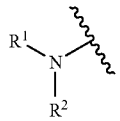

in formula Ie' is selected from the group consisting of

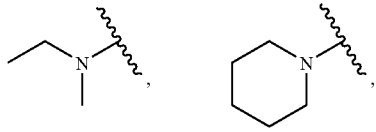

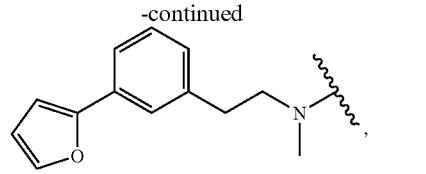

and

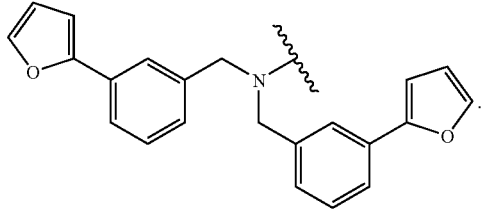

15. A method of inhibiting the proliferation of a bacterial or fungal pathogen, comprising contacting the microbial pathogen with an effective amount of a compound having a structure according to claim 1.

16. A method according to claim 15, wherein the pathogen is selected from the group consisting of *Staphylococcus aureus, Streptococcus pneumoniae, Staphylococcus epidermidis, Enterococcus faecalis,* and *Haemophilus influenzae.*

17. A method of treating an infection by a bacterial or fungal pathogen, comprising administering to a subject suffering from such infection a therapeutically effective amount of a compound having a structure to claim 1.

18. A method according to claim 17, wherein the pathogen is selected from the group consisting of *Staphylococcus aureus, Streptococcus pneumoniae, Staphylococcus epidermidis, Enterococcus faecalis,* and *Haemophilus influenzae.*

19. A method according to claim 18, wherein the subject is a human.

20. A pharmaceutical composition comprising a compound according to claim 1 and an excipient.

* * * * *